United States Patent [19]
Baum et al.

[11] Patent Number: 5,249,121
[45] Date of Patent: Sep. 28, 1993

[54] REMOTE CONTROL CONSOLE FOR SURGICAL CONTROL SYSTEM

[75] Inventors: James P. Baum, DeFiance; John J. Weidenbenner, Manchester; Michael S. Ameiss, O'Fallon, all of Mo.

[73] Assignee: American Cyanamid Company, Stamford, Conn.

[21] Appl. No.: 427,614

[22] Filed: Oct. 27, 1989

[51] Int. Cl.$^5$ .............................. G06F 15/42
[52] U.S. Cl. .................. 364/413.01; 345/4; 345/113
[58] Field of Search ............ 340/716, 717, 734; 364/413.01, 413.02, 413.03, 709.08, 709.09, 709.1; 128/709, 710, 712

[56] References Cited

U.S. PATENT DOCUMENTS

| | | | |
|---|---|---|---|
| Re. 33,229 | 6/1990 | Schwaber | 364/709.01 |
| 4,084,250 | 4/1978 | Albertine et al. | 364/708 |
| 4,559,705 | 12/1985 | Hodge et al. | 340/734 X |
| 4,567,481 | 1/1986 | Meier et al. | 340/784 |
| 4,665,466 | 5/1987 | Green | 361/384 |
| 4,758,925 | 7/1988 | Obata et al. | 361/384 |
| 4,899,254 | 2/1990 | Ferchau et al. | 361/384 |
| 4,933,843 | 6/1990 | Scheller et al. | 364/413.01 |
| 5,091,656 | 2/1992 | Gahn | 307/119 |

FOREIGN PATENT DOCUMENTS

| | | | |
|---|---|---|---|
| 0074642 | 6/1980 | Japan | 340/734 |
| 0146336 | 8/1984 | Japan | 340/716 |
| 0176834 | 10/1984 | Japan | 340/716 |
| 2147126 | 5/1985 | United Kingdom | 340/717 |

*Primary Examiner*—Roy N. Envall, Jr.
*Assistant Examiner*—David Huntley
*Attorney, Agent, or Firm*—Ronald M. Nabozny; Douglas E. Denninger

[57] ABSTRACT

A remote control unit for use with an ophthalmic surgical system having a main control console with video display screen and operator interface. The remote controller is connected by an electrical umbilical cord to the main console and provides a second operator display and membrane-switch interface for use by a surgeon or other member of the surgical team. This remote control unit has its own housing with a splash-resistant front face that is divided into primary and secondary operator interface panels. The primary panel includes a rectangular display field having a plurality of back-illumination lights for selectively illuminating legends found on a replaceable legend card that fits within a slot behind the face plates. Control functions corresponding to the illuminated legends may be selected or deselected by pressing nearby switches arranged in locations adjacent to the display field. The secondary panel also contains membrane switches and legends illuminated by back-lighting. The remote console includes its own microcontroller which electronically receives information from and sends information to the main console via a serial communications interface. Through the use of replaceable legend cards, the remote console is capable of simulating surgical mode and procedure screens which are also displayed upon the CRT screen of the main console.

15 Claims, 13 Drawing Sheets

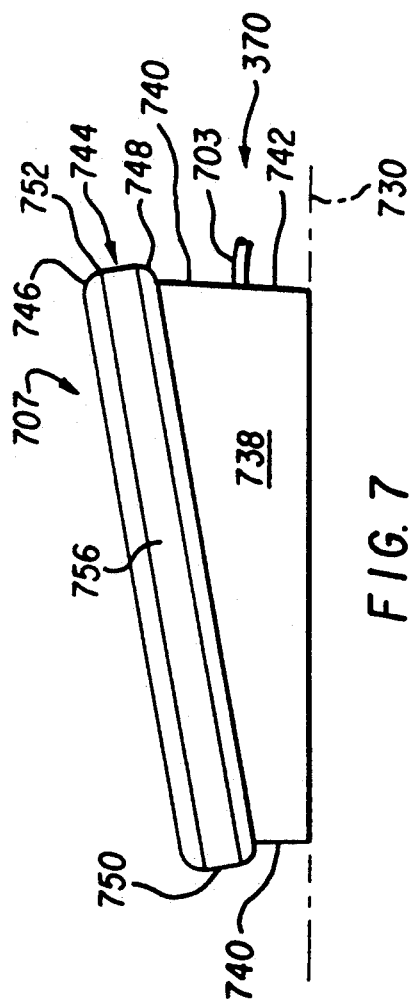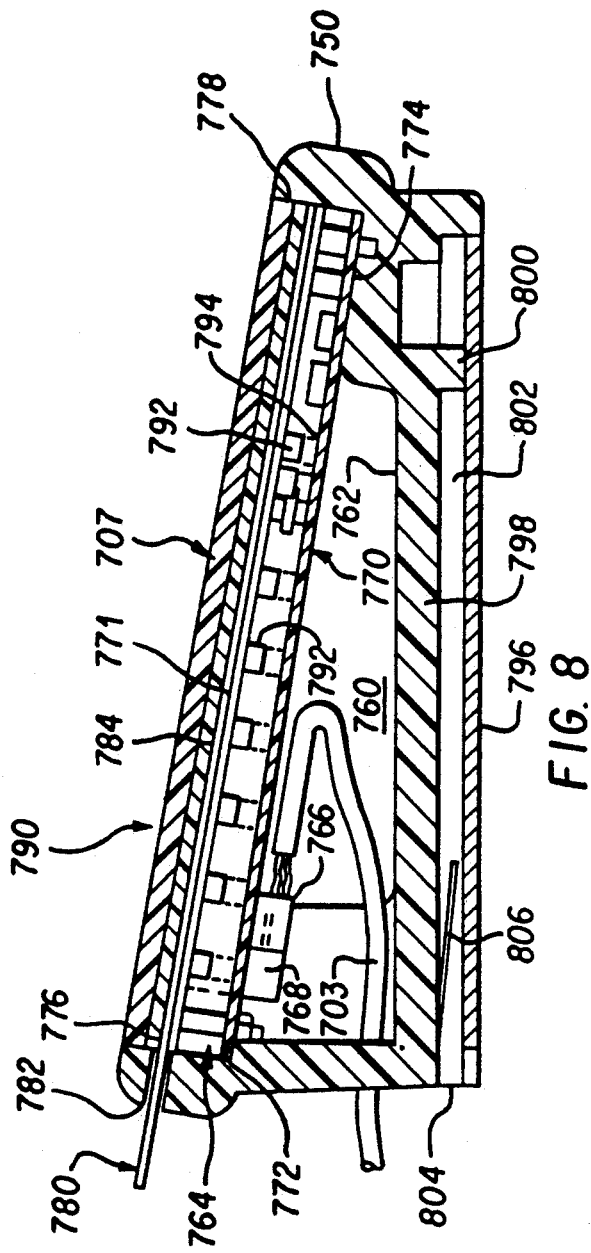

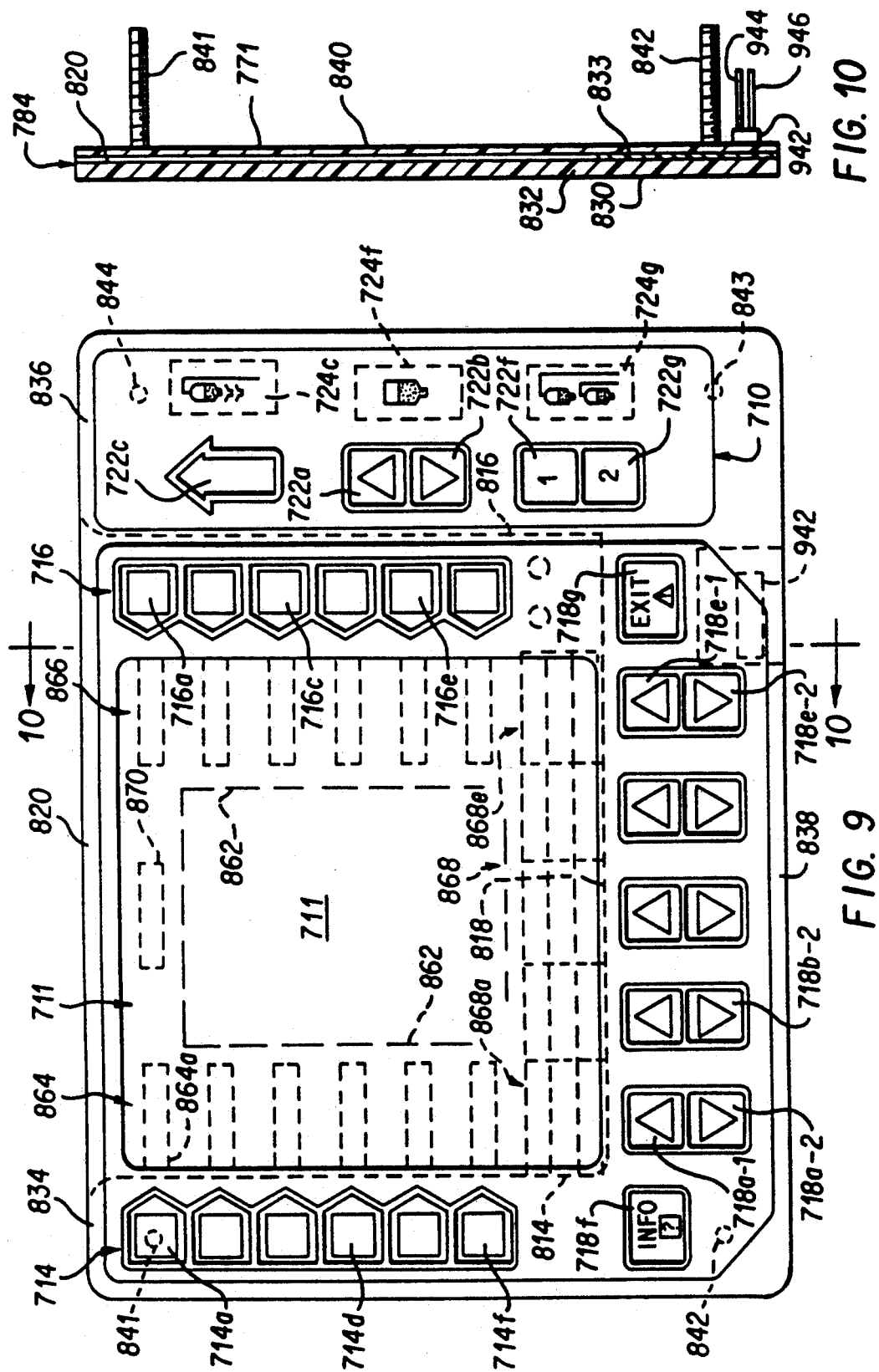

REMOTE CONTROL CONSOLE FOR SURGICAL CONTROL SYSTEM

CROSS-REFERENCE TO RELATED APPLICATIONS

The present invention is related to the subject matter of the following commonly assigned co-pending applications:

Ser. No. 07/267,713 filed Nov. 4, 1988, now U.S. Pat. No. 4,933,843, which is a continuation of application Ser. No. 06/928,170 filed Nov. 6, 1986 now abandoned, and entitled "Control System For Ophthalmic Surgical Instruments."

The present invention is also related to the subject matter of the following commonly assigned applications being filed concurrently on even date herewith:

Application Ser. No. 428,232, filed Oct. 27, 1989 entitled "Control System For Ophthalmic Surgical Instruments", now abandoned;

Application Ser. No. 428,354, filed Oct. 27, 1989, entitled "Control System For Calibrating And Driving Ultrasonic Transducer," now abandoned to form a continuation Ser. No. 07/954,693, Application Ser. No. 428, 125, filed Oct. 27, 1989, now U.S. Pat. No. 5,047,088, issued Sep. 10, 1991, entitled "Vitrectomy Probe".

Application Ser. No. 428,126, filed Oct. 27, 1989 entitled "Modular Cabinet For Surgical Control System", now abandoned;

Application Ser. No. 428,355, field Oct. 27, 1989, now U.S. Pat. No. 5,091,656, issued Feb. 25, 1991; entitled "Footswitch Assembly With Electrically Engaged Detents";

Application Ser. No. 428,166, filed Oct. 27, 1989 now abandoned; entitled "Motorized IV Pole Assembly"; and Application Ser. No. 428,239 filed Oct. 27, 1989 entitled "Pneumatic Controls For Ophthalmic Surgical System".

The disclosures of each and every one of the above-referenced applications is hereby incorporated herein by reference.

BACKGROUND OF THE INVENTION

In the ophthalmic microsurgical art, there are a number of different arrangements known for providing operator interfaces with pneumatic and electronic control consoles used to power and operate microsurgical instruments such as phacoemulsification probes, irrigation needles, air-exchange needles, vitrectomy probes, microsurgical scalpels used in capsular anterior capsulotomy (CAC) procedures, bipolar coagulation electrodes, aspiration needles, and the like. In the past, separate individual control cabinets were provided for the individual pieces of a control equipment required to power operate the one particular instrument, for example, a guillotine-type vitrectomy probe, which requires aspiration and a pulsating pneumatic signal to drive its internal spring-biased piston. Such a control cabinet is typically provided with an adjustment knob for regulating air pressure, another knob for regulating the frequency of the pulsating pneumatic signal, and oftentimes a an LED read-out of the vacuum level used for aspiration, and another LED display in cycles per minute ("cpm") for displaying the cut rate or frequency of the pneumatic driving signal. As another example, it is known to provide a self-contained control module for producing electrical energy at ultrasonic frequencies for driving a phacoemulsification probe. This control module would typically include one or more adjustment knobs for changing the level of electrical input power to the probe, the duty cycle of the electrical signal, and a plurality of LED displays for providing a read-out of pertinent information such as average power level and an elapsed time value indicating the total time ultrasonic energy has been utilized during the surgical procedure. Such phaco probes also normally require aspiration to suction away disintegrated fragments and other debris created by use of the phaco probe, and the supply of irrigation to help wash away such disintegrated fragments.

Thus, in order to have a complete ophthalmic surgical system capable of performing all operations, a hospital or clinic purchased several control modules, each in their own enclosure, which could be used separately or simultaneously, depending upon the requirements of the particular surgical procedure. However, each control cabinet had its own operator interface, with LED displays, dials, knobs and buttons as described above. Each also had its own separate connector or port for plugging in the appropriate instrument cable, tubing line or other needed connector. In this environment, each separate surgical piece of equipment was operating autonomously, at least in a physical sense.

Such pieces of individually designed equipment do not provide a common operator interface for selecting all of these functions. One consequence of this practice was a multiplicity of footpedals, one for each separately controlled instrument. This situation was not entirely satisfactory to surgeons, so a more integrated approach to interfacing various pieces of control equipment evolved. A number of newer systems now provide a footpedal with a plurality of switches mounted thereon so that more than one function can be controlled via a single footpedal.

A few years ago, the assignee of the present invention, namely Storz Instrument Company of St. Louis, Mo. (hereinafter "Storz"), introduced to the market a fully integrated control console for ophthalmic surgery for use in performing almost all types of ophthalmic surgical procedures. This integrated control system and console is sold under the trademark "DAISY" and has enjoyed considerable commercial success. It supported a wide variety of microsurgical instruments. One of the unique features of the DAISY control console is its use of a CRT display with two columns of five membrane-type switches adjacent either vertical side of the display screen and a horizontal row of four endless digital potentiometers adjacent the bottom of the display screen. A slot for an aspirant collection cassette was provided in the lower-front corner of the console, and a horizontal row of instrument connector ports was provided below the row of potentiometers, allowing a variety of microsurgical instruments to be plugged in. A footpedal assembly for use by the surgeon conducting the operation was also provided. The DAISY console also included a pneumatic system for producing aspiration and pulsating pneumatic signals for driving various instruments such as guillotine cutters used in vitrectomies and microscissors used for vitreoretinal operations, and electrical systems for bipolar cautery and phacoemulsification.

Although the DAISY console has been well received, there still remains, on the part of a number of ophthalmic surgeons, a desire to have more "hands-on" control over the surgical control equipment they use. In a typical ophthalmic operation, a surgeon often has the assistance of a scrub nurse and a circulating nurse, and sometimes others. The surgeon spends much time peering through a binocular microscope to obtain a magnified view of the eye being operated upon. Thus, the surgeon typically requests assistance from the nursing staff for activity such as changing pressures, power levels, and cut rates, raising or lowering the IV bottle containing the saline solution used to irrigate the eye, and changing the control modes of the equipment. Under some circumstances, such as a cataract operation where an emergency vitrectomy must be performed, the surgeon may well be involved in completing one task, such as a phacoemulsification procedure, while the other members of the surgical team are busy setting up for a different surgical procedure, such as a vitrectomy. Under such circumstances, it would be extremely useful if there were two separate means for controlling the surgical equipment. A remote control console, particularly one which could provide most of the functionality of the main control console, would be extremely useful.

In other circumstances involving use of the DAISY console, a surgeon may wish to personally select a different surgical procedure at the same time that the assistant needs to read another screen providing instructions for some procedure. Also, the surgeon may wish to change surgical procedures, control modes or parameter settings when the nurses are occupied setting up tools or equipment for the next surgical procedure to be performed. In this situation, a remote control console would also be helpful.

In light of the foregoing needs, it is a primary object of the present invention to provide a remote control console for use in conjunction with a main console of a microsurgical system used to operate microsurgical instruments. It is a related object of the present invention to provide such a remote controller which simulates most of the functionality provided through the operator interface on a main surgical console.

It is a related object of the present invention to provide a remote control console having a display region capable of displaying or illuminating a variety of different messages depending upon the particular surgical procedure being performed. It is a further object to provide a plurality of input switches disposed adjacent such a display region on the remote unit for allowing a user to select different surgical procedures or adjust various controls, and/or parameter settings as desired.

SUMMARY OF THE INVENTION

In light of the foregoing needs, there is provided in accordance with the first aspect of the present invention, a remote operator interface console for use with a microsurgical control system that operates one or several microsurgical instruments and has a main console, a main processor and a display screen for simultaneously displaying multiple fields of information associated with the microsurgical instrument(s). The remote console comprises: communication means, connected to the main processor for causing the remote console to communicate to with the control system; and display means, connected to the communication means, for simulating the display of at least part of the information associated with the microsurgical instruments. The communication means may comprise a serial communications interface and interrupt generation means. The remote console may include a microcontroller and a plurality of light of light emitting means. Further, the console may be provided with card means that can be removably placed over at least some of the light emitting means, for providing legends that are illuminated by passing the emitting light therethrough to simulate the display of the information contained on the display screen.

According to a second aspect of the present invention, there is provided a remote controller for use in conjunction with a microsurgical control system of the type previously described, but also including a plurality of operator interface switches in which the display screen displays information in response to the actuation of the those switches. The remote controller comprises: communication means, connected to the main processor for allowing the control system to communicate information to the remote controller that is to be displayed, and for transmitting to the main processor information entered by a user at the remote controller. The remote controller further comprises input means for enabling the user of the remote controller to enter information to be received by the main processor, and light emitting means, connected to the commutation means, for emitting light therefrom in response to communicated information that is to be displayed. The remote controller further preferably utilizes a plurality of membrane switches or other types of switches arranged in a predetermined pattern which emulates at least part of the pattern in which the operator input switches on the main console are arranged.

The remote display console or controller is also preferably provided with housing means thus connected to and substantially encapsulates the communications means, the interrupt generation means if one is provided, the light emitting means.

These and other aspects, features and advantages of the present invention will be better understood by studying the detailed description in conjunction with the drawings and the accompanying claims.

BRIEF DESCRIPTION OF THE DRAWINGS

The drawings form an integral part of the description of the preferred embodiments and are to be read in conjunction therewith. Like reference numerals designate the same or similar components or features in the various Figures, where:

FIG. 2 is a front view of the FIG. 1 control console showing the lay-out of the CRT visual display, control buttons or keys, surgical instrument connection ports and the like;

FIG. 7 is a right side view of the FIG. 5 unit;

FIG. 8 is a cross-sectional view of the FIG. 5 unit taken along line 8—8 of FIG. 5;

FIG. 9 is an enlarged view of the front of the membrane switch assembly showing the location of the membrane switches in solid lines and for reference the rectangular back-illumination lights in phantom (which are not part of the membrane switch assembly);

FIG. 10 shows a right side view of the membrane switch assembly of FIG. 9;

DETAILED DESCRIPTION OF THE PREFERRED EMBODIMENTS

I. General

A. Front of Control Console (FIG. 1A)

1. Display & Keys Of Primary Panel

Figure 1A:
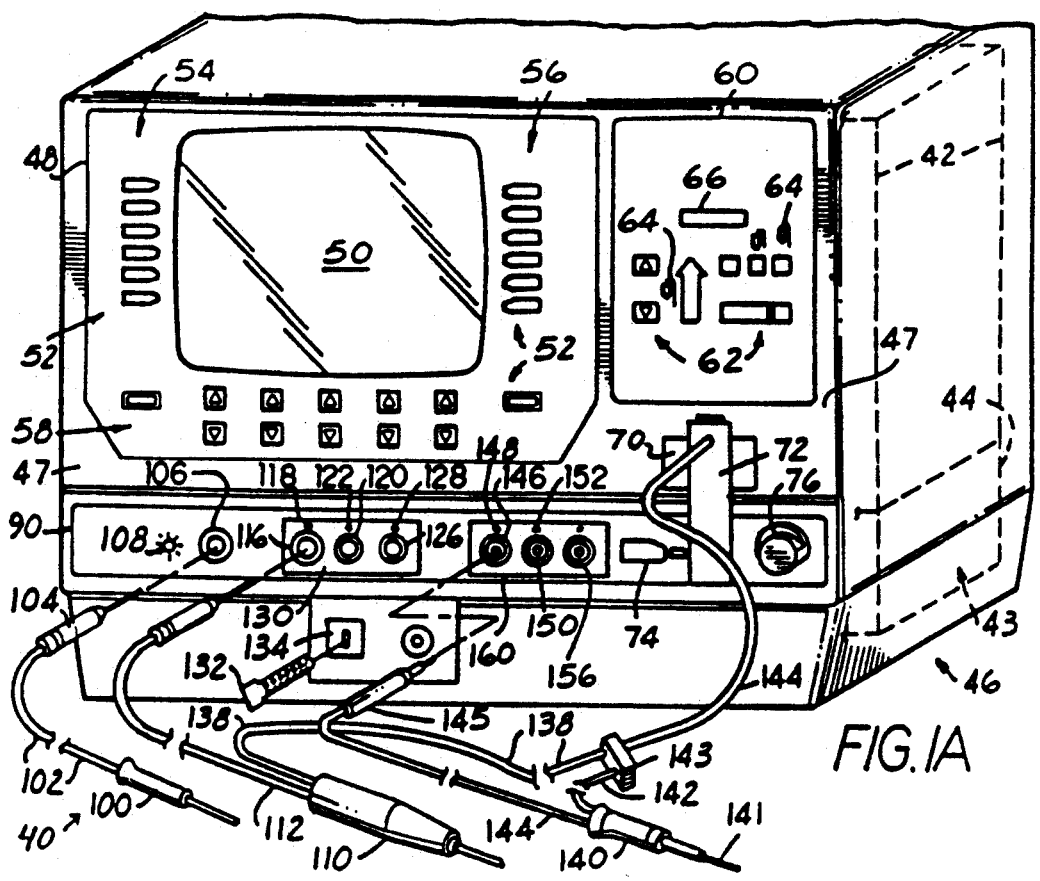
FIGS. 1A and 1B are front and back perspective views of an ophthalmic microsurgical control console which is utilized in the conjunction with the remote control console of the present invention.
Figure 1B:
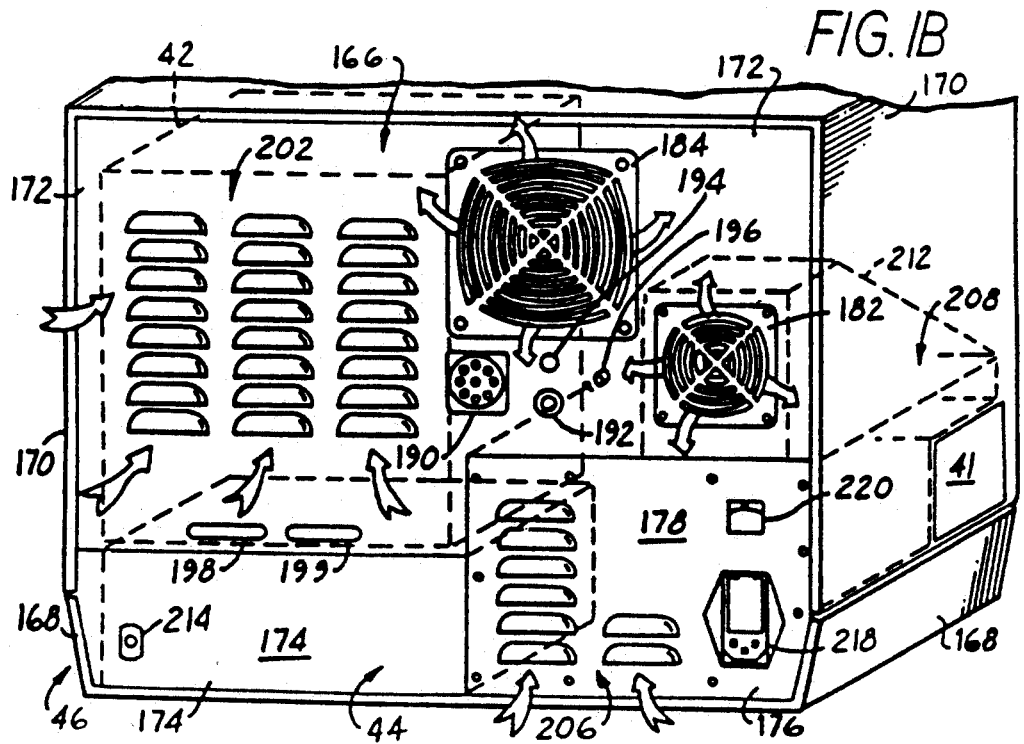
Figure 2:
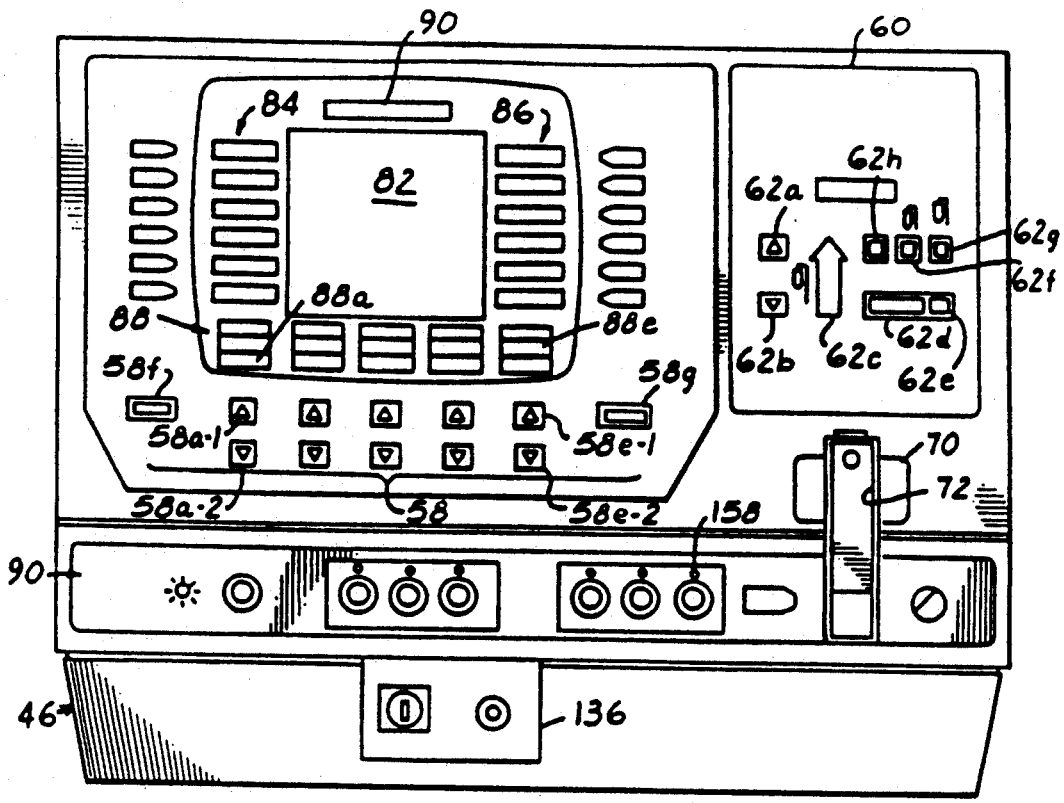

FIGS. 1A, 1B and 2 show a microsurgical control system 40 provided with an illumination lamp drawer 41, an electronic control system housed in part in a nine-board electronic card rack 42, and a pneumatic control system 43 housed primarily in a pneumatic drawer module 44, and other modules which will be described later. The control system 40 includes a system console 46 which has an upwardly and slightly inwardly-sloping front surface 47 with a primary front panel 48. On the front panel 48 is an electronic display screen 50, a plurality of pushbuttons or touch sensitive pads 52 organized in two groups 54 and 56 along the left and right sides of the display screen 50, and a third group 58 along the bottom of the display screen 50. Additionally, there is a secondary front panel 60 located to the right of front panel 48 which has additional pushbuttons or pads 62, indicator lights 64 and information readout 66. The console 46 also includes a slot 70 for a conventional Storz aspirant collection cassette 72, a cassette eject button 74 and an irrigation pinch valve assembly 76.

The electronic display screen 50 is controlled by a microcomputer within the console 46 to provide several different menus or messages which instruct the operator as to the function of the pushbuttons 52 through 62. The operation of the display screen 50 in combination with the buttons 52-62 may be best understood by looking at the enlarged view in FIG. 2. The display screen 50 is shown there as being conceptually divided into central display screen region 82, left-side display region 84, right-side display region 86, bottom display region 88 and a top display region 90. The side regions 84 and 86 each consist of six horizontal fields stacked one above the other and positioned to correspond to the locations of buttons in button groups 54 and 56. By virtue of the adjacent location of the top button of button group 54 and the top field of region 84, for example, a message in the upper left-hand corner of the screen 50, i.e., in this top field, is readily understood by the operator as referring to the upper leftmost button. The other buttons and fields are similarly paired. This arrangement allows the indicated function of each of the buttons 54 or 56 to be readily changed by simply just changing the legend displayed in its adjacent field. In a similar manner, each pair of buttons, such as buttons 58a-1 and 58a-2, is associated with one of the three-part fields of bottom region 88, such as region 88a. In general, the upper row of buttons, i.e., buttons 58a-1 through 58e-1 are used to increment a setting or parameter displayed in the corresponding region 88a-88e of screen 50 directly above, while the buttons in the lower row, i.e., buttons 58a-2 through 58e-2, are used to decrement such displayed settings or parameters. The use of an electronic display screen also permits the legends for buttons 52, 54 and 56 to be labeled in virtually any language. Button 58f is used to bring up an information screen on display 50 to assist the operator, such as by further explaining functions associated with choices on the display menu. Button 58g is used to return to an earlier menu screen in a chain of related menus or other screens.

2. Surgical Instrument Connector Panel

The microsurgical control system 40 is capable of operating a number of different microsurgical instruments. To provide for this functionality, there is a row of different types of connector receptacles on surgical instrument connector panel 90 which permits various instruments to be plugged in or otherwise controlled by the control system 40 as may be seen in FIGS. 1A and 2, indicator lights are provided adjacent to or above each of the connector receptacles for indicating when the connector is activated or functional.

a. Illumination Instrument

FIG. 1A shows a fiber-optic illumination instrument 100 coupled to console 46 via fiber-optic cable 102 which extends out of male illumination connector plug 104 designed for insertion into illumination connector receptacle 106. Indicator lamp 108 is illuminated whenever the fiber optic illumination (FOL) lamp inside console 46 is lit.

b. Electrically Powered Instruments

Phaco fragmentation handpiece 110 is a conventional piezoelectric device for disintegrating hard objects such as intraocular cataractous material utilizing ultrasonic ("US") energy transmitted to its needle 112. Electrical power pulsating at US frequency is provided to handpiece 110 via power cable 112 attached to phaco connector plug 114, which is designed to be inserted into phaco female connector 116. Light 118 indicates when US frequency electrical power is being delivered to 116. Female connector 120 is designed to receive a male connector plug 120 for powering a conventional bipolar coagulator handpiece. Indicator light 122 indicates when this connector 120 is operational. Female connector 126 is used for receiving a male connector plug (not shown) of a conventional CAC handpiece. (CAC stands for "controlled anterior capsulotomy.") Indicator 128 illuminates when the CAC function is activated. Thus it will be seen that the three connectors 116, 120 and 126 grouped together on rectangular plate 130 all relate to electrically powered surgical functions.

c. Fluid-Powered Instruments

Certain microsurgical instruments are actuated or controlled by fluid pressure (either positive pressure or negative pressure, or both). The phaco fragmentation instrument 110, for example, utilizes aspiration through hollow flexible plastic tubing 138 to remove disintegrated materials, which are collected along with aspirant in the cassette 72.

Vitrectomy probe 140 includes a hollow needle 141 having an inner tube which reciprocates to cut intraocular material sucked in a small hole near the tip of the needle. The inner tube (not shown) reciprocates on account of pulsating air pneumatic drive signal delivered to a spring-returned piston (not shown) to which the inner tube is connected. The suction part of this instrument is also coupled to the collection container 72 by tubing 142. (Bracket 143 is intended to indicate that either tube 142 or tube 138 may be connected to the remaining portion of tube 144 which leads to the collection cassette 72.) Tubing 144 extending from the probe 140 leads to male connector plug 45 which is inserted into vitrectomy connector receptacle 146. Light 148 indicates when the connector is activated. Connector 146 supplies the pulsating air drive signal to the vitrectomy probe from a pneumatic circuit which will later be described. A conventional vitrectomy probe in the form of a guillotine cutter such as the Storz Microvit probe may be used. Alternatively, the improved probe described in aforementioned application Ser. No. 07/428,125, now U.S. Pat. No. 5,047,008, entitled "Vitrectomy Probe" may be used as probe 140.

Connector receptacle 150 provides access to an intraocular pressure (IOP) system, and indicator light 152 indicates when connector 150 is actuated. Connector 156 is used to deliver a pneumatic drive signal to conventional pneumatically operated microscissors (not shown), which can be operated in any one of three modes as will be further explained. Indicator light 158 is illuminated when any one of the three scissors modes is enabled. In light of the foregoing description, it will be appreciated that the three connectors 146, 150 and 156 located on rectangular plate 160 all relate to surgical functions implemented via the pneumatic system of console 46.

While certain microsurgical instruments have been illustrated or described in connection with FIG. 1A, it should be understood that the microsurgical control system 40 can be used with other instruments of a similar type. In general, any microsurgical instrument that is actuated or controlled by fluid pressure (whether positive or negative), can be made to operate with the pneumatic control system of the present invention.

d. Irrigation Pinch Valve

The irrigation pinch valve assembly 76 is utilized to provide on/off control for the gravity-infused salt solution held in the IV bottle. The pinch valve is operated by an on/off solenoid of the pneumatic system as will be further explained. Display 66, which may be an LED display or the like, indicates the height of the IV pole above the minimum reference height established via the zero switch 62e.

3. Off-line Memory Storage of User Data,

On occasion, it is desirable to store selected operating values or set-up parameters for a particular surgeon or microsurgical operation in off-line memory. A removable memory key 132 is provided for this purpose. The key 132 includes an integrated memory circuit which stores such operating values or set-up parameters. Console 46 receives the key 132 through a key receptacle interface 134 mounted in plate 136. Suitable types of memory keys and receptacle interfaces are commercially manufactured by Datakey, Inc. of Burnsville, Minn. However, it should be appreciated that other suitable means for storing particular user data may be employed with the console 46 as well, such as electronic cards with memory, magnetic disk media, or the like.

4. Display & Keys Of Secondary Panel (FIG. 2)

The functions associated with the secondary panel 60 will now be described. As best seen in FIG. 2, panel 60 is used to control a motorized IV pole (not shown) that supports one or more bottles or pouches of balanced salt solution used to provide irrigation during ophthalmic surgical procedures. The motorized IV pole includes a reversible electric motor/gear reducer combination which adjusts the height of the IV pole up or down as desired. The particular height may be selected via the buttons on control panel 60. Buttons 62a and 62b are used to lower and raise the pole incrementally, as long as the button is held. Button 62c is used, under emergency conditions, to send the pole upward rapidly at roughly twice the speed of button 722a as long as the button is held. Button 62d, when depressed, automatically lowers the IV pole to a convenient height to facilitate changing of the IV bottle. Button 62e is called the "zero switch" because when pressed it establishes the zero reference, i.e., the minimum height for the IV pole. Button 62f and 62g are used respectively to change the height for the IV pole to either a first or second preset level. Button 62h is used during set-up to specify the first and second preset heights of the IV pole. The operation of these functions and the construction of the "Motorized IV Pole Assembly" is described in aforementioned application Ser. No. 07/428,166, now abandoned, of the same title.

B. Rear of Control Console (FIG. 1B)

FIG. 1B shows the rear of the system console 46, including the rear surface 166. The console 46 includes a base frame or chassis 168, a sheet metal cover 170 having three sides forming an inverted U-shape, and back cover plate 172 occupying roughly the top two-thirds of the surface 166. The bottom one-third of the rear surface 166 is occupied by the rear wall 174 of pneumatic drawer module 44 shown in phantom, and the rear wall 176 of electrical power drawer 178 which is also partially shown in phantom and will be later described. Mounted on the upper rear cover plate 172 are the following devices: small ventilation fan 182, a large ventilation fan 184, an electrical connector receptacle 190 for a footpedal controller, an IV pole connector receptacle 192, an accessory connector receptacle 194 and a CRT screen brightness control knob 196. Cover slots 198 and 199 are also provided for future expansion to allow addition of RS232 communication ports. Rear cover plate 172 includes a set 202 of 24 ventilation louvers arranged in three columns. Rear wall 176 of power electrical drawer 178 includes a set 206 of eight ventilation louvers arranged as shown. Both sets 202 and 206 of louvers allow air to be drawn inside of the console 46. Air drawn in through louvers 202 circulates internally and eventually exits at exhaust fan 184, while air drawn in through louvers 206 is substantially confined to circulate within the electrical drawer 178 and past the lamp drawer 41 since it is confined by shelf/cover 208 and plenum 212 to be exhausted by ventilation fan 182.

The main pneumatics supply connection to pneumatics drawer 44 is made through a male Schrader quick-disconnect fitting 214 in the lower left rear corner of rear wall 174. Electrical power is provided to the electrical drawer module 178 via electrical receptacle and fuse holder assembly 218. A main on/off electrical power switch 220 for turning the console 46 on or off, is located above receptacle 218. The various hardware assemblies and drawers of console 46 are constructed in a highly modular, easy-to-assemble and easy-to-service manner described in detail in aforementioned application Ser. No. 07/428,216, now abandoned, entitled "Modular Cabinet For Surgical Control System."

II. Surgical Modes & User Interface In General

A. Switch-Selectable Surgical Modes & Features

The control console 46 is the heart and brain of the multi-function microsurgical system 40. The system 40 supports up to nine switch-selectable modes which are used in either or both anterior segment and posterior segment ophthalmic surgery. These modes are: (1) irrigation only, (2) irrigation/aspiration, (3) phaco (either emulsification or fragmentation), (4) vitrectomy, (5) controlled anterior capsulotomy (CAC), (6) bipolar, (7) scissors, (8) illumination, and (9) intraocular pressure (IOP) control. Each mode is automatically integrated into the system 40 in a manner appropriate to the type of operation selected by the operator via keys 52–58.

1. Irrigation mode employs a footpedal on/off control of irrigation. This operating mode is intended for use during an anterior capsulotomy and other anterior segment procedures in which irrigation without aspiration is desired.

2. Irrigation/aspiration mode provides footpedal on/off control over irrigation and linear footpedal control over aspiration. This mode is intended for use in the engagement, stripping and removing of residual lens cortical material in extracapsular cataract extraction and phacoemulsification procedures.

3. Phaco mode implements the phacoemulsification and phacofragmentation functions, which are available for both anterior and posterior segment procedures. Under phacoemulsification procedures, a "fixed phaco" mode is available in which the phaco power and aspiration levels are set via the console controls, and "linear phaco" mode is available in which phaco power is footpedal controlled and aspiration level is determined by the console controls. For phaco fragmentation procedures, a fixed phaco mode controls aspiration via the footpedal.

4. Vitrectomy mode makes the vitrectomy function available for both anterior and posterior segment procedures. For anterior vitrectomy, footpedal on/off control is provided for vitreous cutting and irrigation, while linear footpedal control is provided for aspiration. For posterior vitrectomy, this mode provides footpedal/on-off control over vitreous cutting and linear footpedal control over aspiration.

5. CAC mode provides footswitch on/off control of a CAC probe, and is explained further in connection with the discussion of FIG. 4D below.

6. Bipolar mode provides on/off control of bipolar power via the footpedal assembly, and is described further in the discussion of FIG. 4D below.

7. Scissors mode enables the posterior surgeon to employ a pneumatically driven intraocular scissors in any one of three foot-pedal controlled cutting operations: single cut, variable rate or proportional, which will be explained in more detail later.

8. Illumination mode provides fiber-optic illumination to facilitate viewing the posterior segment during posterior procedures. The light source thereof is adjustable from approximately five-percent illumination to full brilliance. Automatic lamp switching provides back-up illumination if the primary lamp should fail.

9. IOP mode provides precision regulated console-adjusted delivery of filtered air to the eye during posterior ocular pressure procedures. Alternatively this mode can be used to pressurize an irrigation supply to the eye for anterior procedures.

Many of the foregoing modes and features are also found in the Storz DAISY console. For example, like DAISY console, console 46 uses a disposable transparent cassette to collect aspirant during surgery. When the cassette is fully inserted into the cutout slot 70 in the console 46, the system 40 will automatically secure the cassette via a solenoid-actuated valve, and a vacuum connection will be established at that time.

10. Additional Surgical Features. The system 40 also includes additional features, namely, aspiration prime and irrigation prime in the same manner implemented in the DAISY console. Further, the special repeat reflux procedure is supported by the control console 46 in order to allow a handpiece to be cleared with pneumatic pressure if it becomes clogged with tissue. This reflux feature is available in all anterior modes, and consists of repeated reflux action.

B. User Interface Strategy

The integration of all of the aforementioned functions into a single console 46 represents a formidable organizational challenge since the system 40 must provide the operator(s) with a straightforward means of invoking all of the different modes, the functions under each mode, and a way to adjust the various set-up and operating parameters associated with various electronic control circuits and pneumatic control systems. The CRT display and pushbutton arrangement assists system flexibility greatly in this regard since it is possible to reprogram the functions of the switches 52 in accordance with the selected anterior segment or posterior segment procedure or with the selected utility functions, such as establishing set-up values or configuring the system for a particular surgeon's use.

Similarly, the use of a microprocessor-based control system, described in FIG. 4, enables the various strategies for the control functions to be stored in memory and called upon as required. To reduce cost of construction and assembly time, to increase reliability and serviceability, the various components of the surgical system have been constructed as separate modules or subassemblies where possible. This approach is evident in the electronics portion and pneumatics portion of the control system 40. Where practical, distinct electrical functions have been placed on their own printed circuit board which is separately addressed by the microprocessor. Similarly, the pneumatics functions have been collected and placed in one drawer module to allow easy installation and replacement.

III. Footswitch Assembly (FIG. 3)

Figure 3:
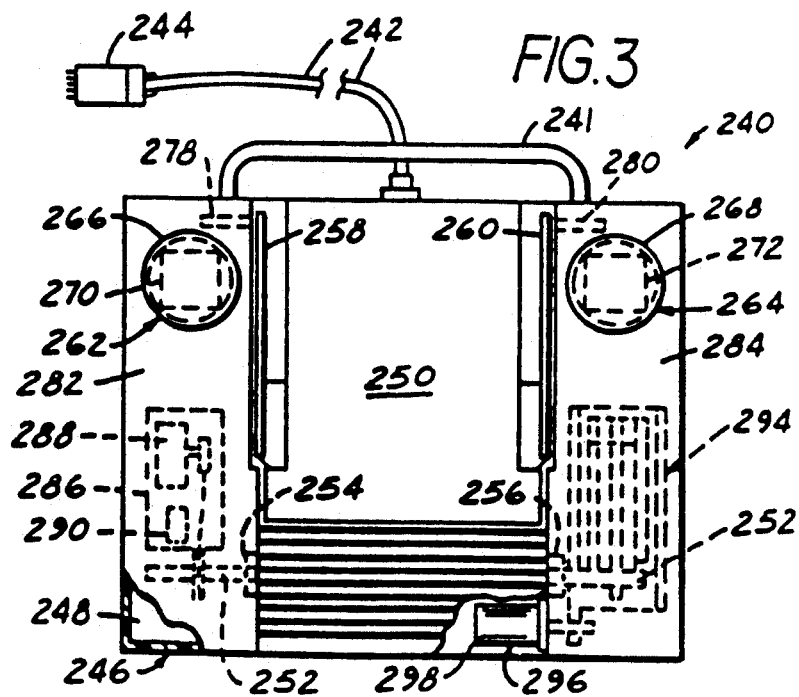
FIG. 3 is a plan view of a footswitch assembly usable in conjunction with the consoles of the present invention.

FIG. 3 shows a plan view of foot controller 240 (also called a footswitch assembly) utilized by the system 40 which has a metal carrying handle 241 and is linked directly to the console 46 with a suitable length of multi-conductor electrical cable 242 which has suitable multi-pin connector 244 at the end thereof that plugs into connector receptacle 190 on the back of the console 46. The footswitch assembly 240 includes: a large plastic molded housing 246 enclosed with a large rectangular bottom plate 248; having a footpedal 250 which pivots about a horizontal footpedal shaft 252 supported by sintered bronze flange bushing assemblies 254 and 256; left and right vertically arranged side pedals 258 and 260; and left and right top footswitch assemblies 262 and 264 having mushroom heads 266 and 268 and electrical contact blocks 270 and 272, shown in phantom, to signal when the respective top buttons have been pushed. Side switches 278 and 280, shown in phantom, which may be microswitches or magnetic proximity switches, are actuated and provide electrical signals indicating when their respective side pedals 258 or 260 have been pressed. The housing 246 includes left and right bunker structures 282 and 284 which rise above footpedal 250 upon which top footswitches 262 and 264 are mounted. Underneath left bunker 282 is located a footpedal position encoder assembly 286 shown schematically in phantom. Assembly 286 includes an optical position encoder 288 which produces two digital signals in a quadrature relationship as the shaft 252 rotates, and a zero reset switch 290. Under bunker 284 is located a detent assembly 294 which may be electrically engaged as desired via detent control solenoid assembly 296 including an electrical solenoid coil 298. The side switches 278 and 280 and top footswitches 266 and 268 provide on-off control of certain features during selected ophthalmic procedures. For example, the left top footswitch 266 provides on/off control of bipolar coagulation. The right top footswitch 268, via display 50 and buttons 52, may be configured to control the emergency rapid-up feature of the motorized IV pole option or to control some other operating room device via the accessory receptacle 194 on the back cover 166 of console 46. In anterior segment procedures, the footpedal is used to control irrigation, aspiration, phaco and vitrectomy modes in a manner like that used for the Storz DAISY console. However, the footpedal detents are new and are provided in the manner described in aforementioned application Ser. No. 07/428,355, now U.S. Pat. No. 5,091,656, to provide the surgeon with tactile feedback regarding the footpedal position. Further details of the construction and operation of the footpedal assembly 240 are given in aforementioned application Ser. No. 07/428,355, now U.S. Pat. No. 5,091,656, entitled "Footswitch Assembly With Electrically Engaged Detents."

IV. Electronic Control System (FIG. 4)

A. General Overview of Electronics Hardware (FIG. 4A)

Figure 4A:
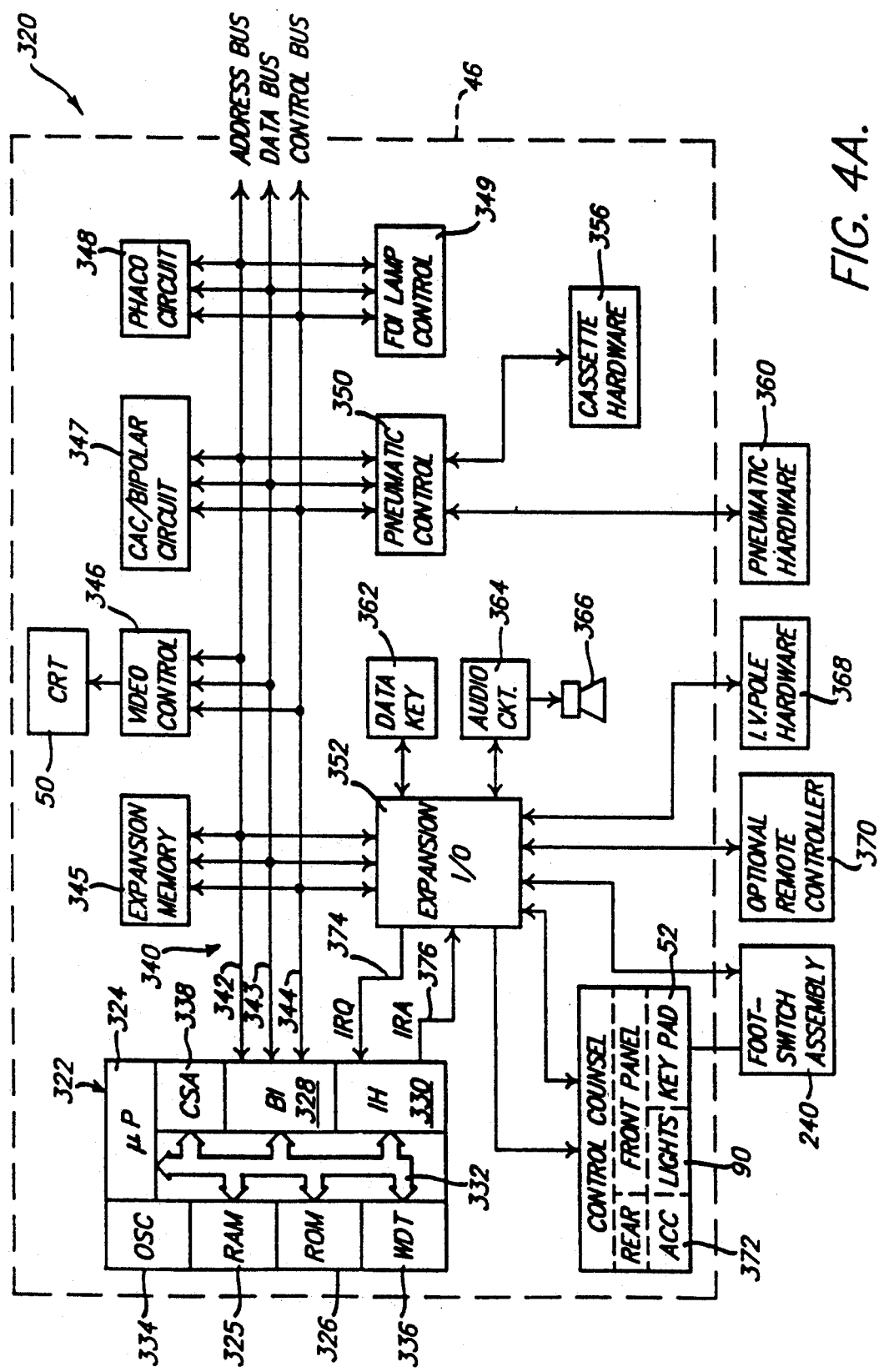
FIG. 4A is a simplified block diagram of the microprocessor-based electronic control system of the FIG. 1 control console showing how information is passed electronically between the microprocessor and the various boards and devices within the over-all surgical system.

FIG. 4A shows a simplified block diagram of a microprocessor-based electronic control system 320 found in the control console 46 shown in FIG. 1. Control system 320 includes a microcomputer 322 having a microprocessor 324, volatile (RAM) memory 325, nonvolatile (ROM) memory 326, a VME bus interface circuit or port 328, an interrupt handling circuit or port 330, and an internal control/address/data bus 332 which allows internal communications in conventional fashion between all portions of microcomputer 322. A preferred microprocessor 324 is a 68000 Series Motorola microprocessor with a clock speed of 12.5 Megahertz and one wait state for handling interrupts, although any other suitable microprocessor could be used. Computer 322 also includes a 25 Megahertz crystal oscillator 334, a watchdog timer circuit 336, and a chip select and addressing (CSA) section 338. The microcomputer 322 is located on a single board, called the processor board.

The microcomputer 322 which is located on its own printed circuit (PC) board, communicates with the remainder of the electronic control system 320 via a VME bus 340 consisting of address, data and control lines 342, 344 and 346. The VME bus 340 is used to communicate with seven other boards within the system 320, namely: the expansion memory PC board 345, the video control PC board 346 which drives the visual display 50, the CAC/bipolar circuit PC board 347, the phaco circuit PC board 348, the lamp control PC board 349, the pneumatic control PC board 350, and the expansion I/O PC board 352.

The groupings of various functions on distinct PC boards was done in order to make maintenance simpler. By clustering similar or related functions together on one board, it is possible to reduce diagnostic time and service costs since individual functions not performing correctly may be isolated on a board-by-board basis, and suspect boards may be replaced as needed. The processor board 322, the expansion memory board 345 and the video board 346 are all conventional purchased items from PEP Modular Computers GmbH of Kaufbeuren, West Germany. The manner in which all of these boards are designed and work from a hardware and operating system perspective is conventional. The manner in which the video board 346 drives the CRT 50 is conventional too. The CRT 50 used with the control console 46 is preferably a 9-inch diagonal monochrome monitor with standard resolution, although any other suitable two-dimensional display may be utilized such as liquid crystal display or electro luminescent display.

The lamp control board 349 is used to control the components in the lamp drawer 41 which is the source of light for fiber optic light pipe 100 shown in FIG. 1A. Pneumatic control board 350 is used to control the cassette hardware 356 and the pneumatic drawer hardware 360. The cassette hardware 356 refers to those input devices such as switches and output devices such as solenoids associated with the aspirant collection cassette 72 shown in FIG. 1A. The pneumatic hardware includes pressure transducer, a torque motor servovalve and solenoids.

Expansion I/O board 352 is used to communicate or control the memory key circuit 362, the audio generator circuit 364, which drives speaker 366, the IV pole hardware 368, an optional remote controller 370, and the footpedal assembly 240 of FIG. 2. The expansion I/O board 352 also is used to interrogate or operate various other input and output devices associated with the control console 46, such as the keypads 52, the indicator lights on secondary panel 60 and connector panel 90 and the accessory relay 372 associated with accessory receptacle 194 shown in FIG. 1A. All user-generated input commands are handled through I/O board 352. To ensure such commands are promptly communicated to the processor 324, board 352 generates an interrupt request (IRQ) signal on line 374 to inform the processor 324 that the I/O board needs to be serviced. The processor also generates an interrupt acknowledge (IRA) signal on line 376. In this manner, user input commands take precedence over lower priority I/O tasks also being handled via VME bus 340.

B. CAC/Bipolar Circuit (FIG. 4B)

Figure 4B:
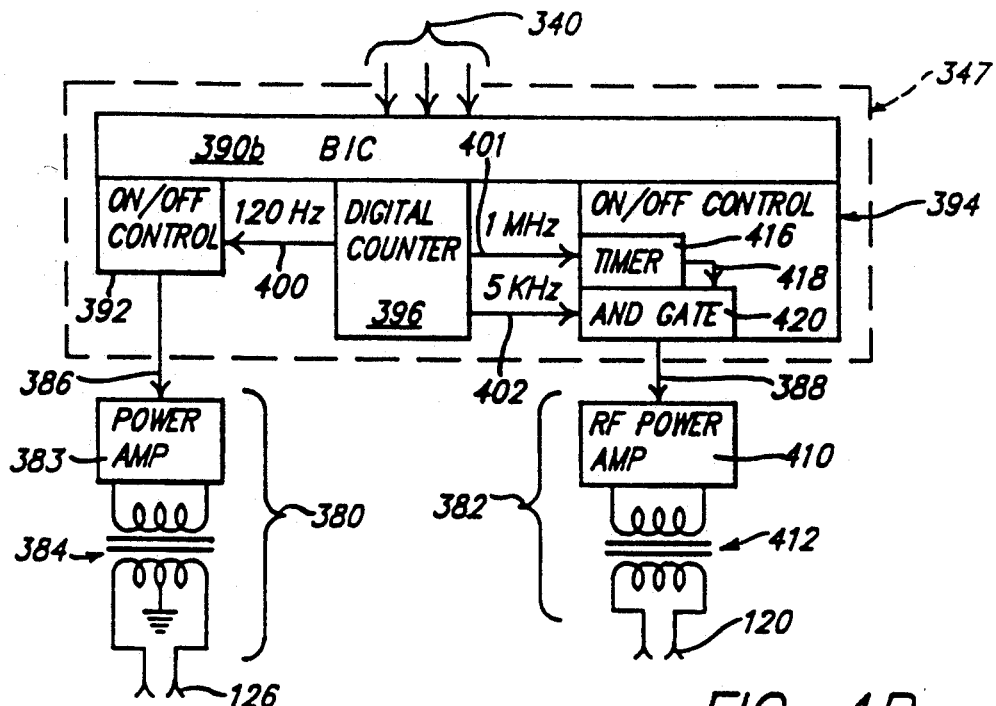
FIG. 4B is a detailed block diagram of the operation of the CAC/bipolar board and equipment of the FIG. 1 control console.

FIG. 4B is a detailed block diagram of the CAC/-bipolar circuit board and the power amplifier/transformer sections 380 and 382 which it drives with DC level control signals 386 and 388. The board 347 includes a standard VME bus interface circuit (BIC) 390b, which is interfaced directly to on/off control circuits 392 and 394 and to a multi-stage digital counter 396. The digital counter 396 is continuously run, and taps are provided at various stages thereof to provide three digital logic level, timebase signals, all of which are square waves having a 50% duty cycle, namely a 120 Hz signal on line 400, a 1 MHz signal on line 401 and a 5 KHz signal on line 402.

CAC function is best understood by explaining a few basics about the capsular anterior capsulotomy procedure. During this procedure, a pyramidally-shaped tip positioned at a right angle to and near the tip of a microsurgical needle vibrates at a fixed rate, such as 120 Hz, in two dimensions, namely axially and transversely. This cutting action is used to cut the anterior capsule of the eye. Upon receiving an appropriate command from the processor 324 over the VME bus 340, on/off control 392 allows this signal 400 to pass through to line 386. Power amplifier 383 amplifies digital signal 386 to approximately 2 watts and transformer 384 converts the output signal from the power amp 383 to a square wave which varies between plus and minus 3.5 volts. The amplitude and frequency are fixed. The power from the secondary transformer 384 is applied to connector 126 on receptacle panel 90 of the console 46. A conventional CAC probe from Storz may be plugged into connector 126.

The bipolar cautery function implemented by the board 347 is conventional, and has been used in the Storz DAISY console several years. In bipolar cautery, a high frequency moderate power signal is applied to electrodes located at the tips of a conventional bipolar probe. The high frequency electrical signal is used to cauterize severed blood vessels, incisions and the like. In the preferred embodiment, a 1 MHz power RF signal is output to connection 120 by RF power amplifier 410 and step-up transformer 412. The maximum output may be limited to 7.5 watts at 100 ohms. The power of the RF signal applied to connector 120 is preferably adjustable from zero to 100 percent. In the electronic control system 320, this is implemented in the following manner. First, the bipolar signal applied to connector 120 is considered to be at 100 percent power when the RF signal is modulated so as to be on 50 percent of the time and off 50 percent of the time. The low level 1 MHz signal 401 is pulse width modulated by on/off control 394 using the 5 KHz signal 402 as a time base. The signal 402 has a 50 percent duty cycle, which means it is on for 100 microseconds and off for 100 microseconds each cycle. This represents 100 percent bipolar power. To reduce the power level, a digital timer circuit 416 within the on/off control 394 reduces the on time of signal 402 while increasing the off time, thus resulting in a pulse width modulated (PWM) signal 418 having a duty cycle corresponding to the duty cycle required to achieve the desired power level. This signal 418 is applied to gate circuit 420 resulting in signal 388 being a PWM composite RF signal which when on oscillates at 1 MHz. Signal 388 is fed to RF power amplifier 410, whose output drives the primary of transformer 412. Transformer 412 isolates the amplifier 410 and provides proper output impedance levels at its secondary. On/off control block 394 thus regulates when the composite RF signal 388 is on, and its effective duty cycle.

C. Phaco Calibration & Drive Circuit (FIG. 4C)

Figure 4C:
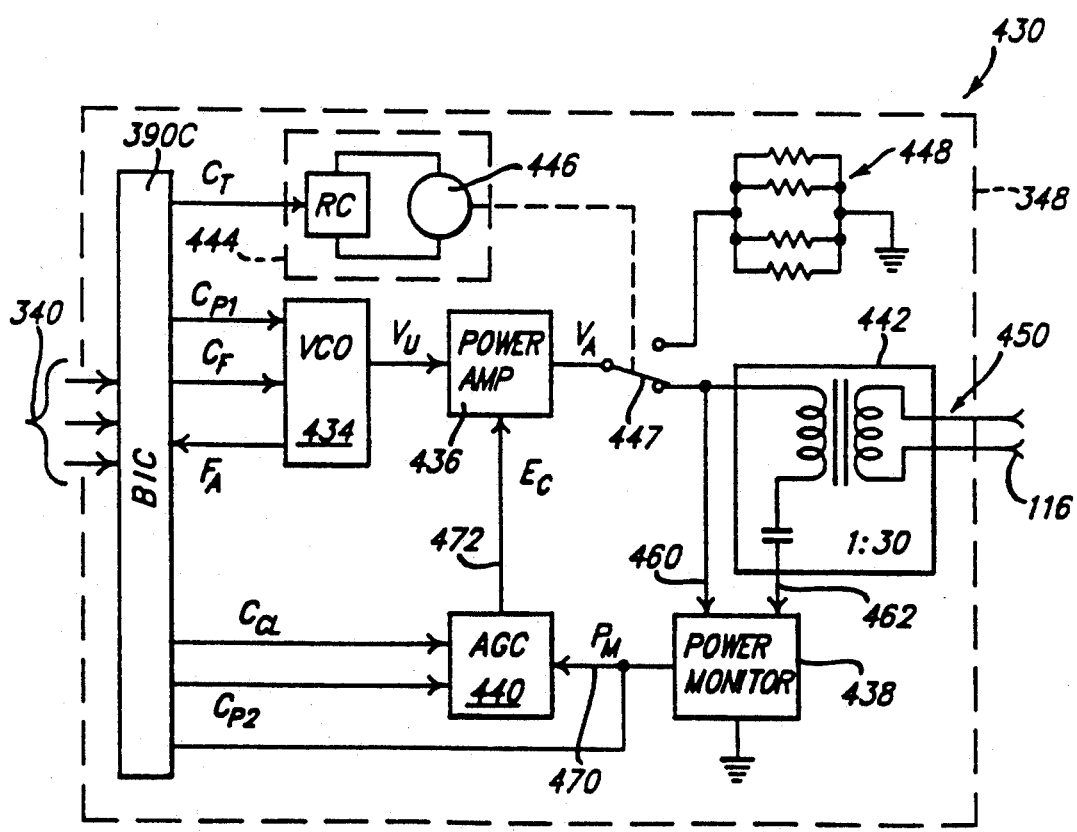
FIG. 4C is a detailed block diagram of the calibration and drive system for a phaco probe.

FIG. 4C shows a detailed block diagram for the phaco circuit 430 forming part of electronic control system 320. The phaco circuit includes another standard VME BIC 390c, which is used to produce a variety of digital control signals including the test command signal $C_T$, a first power command signal $C_{P1}$, a closed loop command signal $C_{CL}$ and a second power command signal $C_{P2}$. The phaco control module includes a voltage controlled oscillator (VCO) section 434, a power amplifier section 436, a power monitor section 438, an automatic gain control (AGC) section 440, a transformer section 442, a relay control section 444 including relay coil 446 which operates a Form-C electrical contact 447 and a resistor bank 448. The phaco drive circuit 430 produces an ultrasonic (US) signal 450 which ranges in strength between 0 and 35 watts at a frequency in the range of 26 KHz to 31 KHz at approximately 5 kilo-ohms. This ultrasonic signal is applied to connector 116 of the receptacle panel 90 of console 46. A conventional phacoemulsification or phaco fragmentation probe may be provided power by plugging its electrical jack 114 into receptacle 116.

In operation, the phaco drive circuits 430 checks itself by having relay section 444 switch the contact 447 to its opposite position, thus applying the US signal from power amplifier 436 to resistor bank 448. Next, circuit 430 switches relay coil 446 off, thus allowing power to flow from amplifier 436 through contact 447 to transformer section 442. At this time the dominant resonant frequency of the ultrasonic transducer is determined by monitoring the voltage and currents signals on conductors 460 and 462 as a US test signal $V_A$ is swept through frequencies within the range of 26 KHz to 32 KHz. During this time, processor 324 looks for power peaks, among other things, to find the resonant frequency. Once the dominant resonant frequency of the transducer/probe plugged into connector 116 is determined, the phaco drive circuit 430 enters a drive mode. In this mode, the circuit 430, under user commands interpreted by processor 324 and delivered via VME bus 340, drives the VCO section 434 at the dominant resonant frequency and desired power level indicated by commands CF and $C_{P1}$, which is passed along as a voltage signal $V_u$ to power amplifier 436, where it is amplified and transferred as signal $V_A$ to transformer section 442. Power monitor section 438 observes the voltage and current applied to the primary of transformer section 442, and produces the monitored power signal $P_M$ on line 470, which feeds into AGC section 440 where it is compared against the desired power command $C_{P2}$. Any deviation between the power desired and the monitored power results in a non-zero error correction signal $E_c$ on line 472, which alters the gain of power amplifier 436 to compensate for and eliminate this error. In this manner, constant power operation of the ultrasonic transduce/probe combination plugged into receptacle 116 is assured. Further details of the operation of phaco drive circuit 430 are set forth in aforementioned application Ser. No. 07/428,354 entitled "Control System For Calibrating And Driving Ultrasonic Transducer."

D. FOI Lamp Control Circuit (FIG. 4D)

Figure 4D:
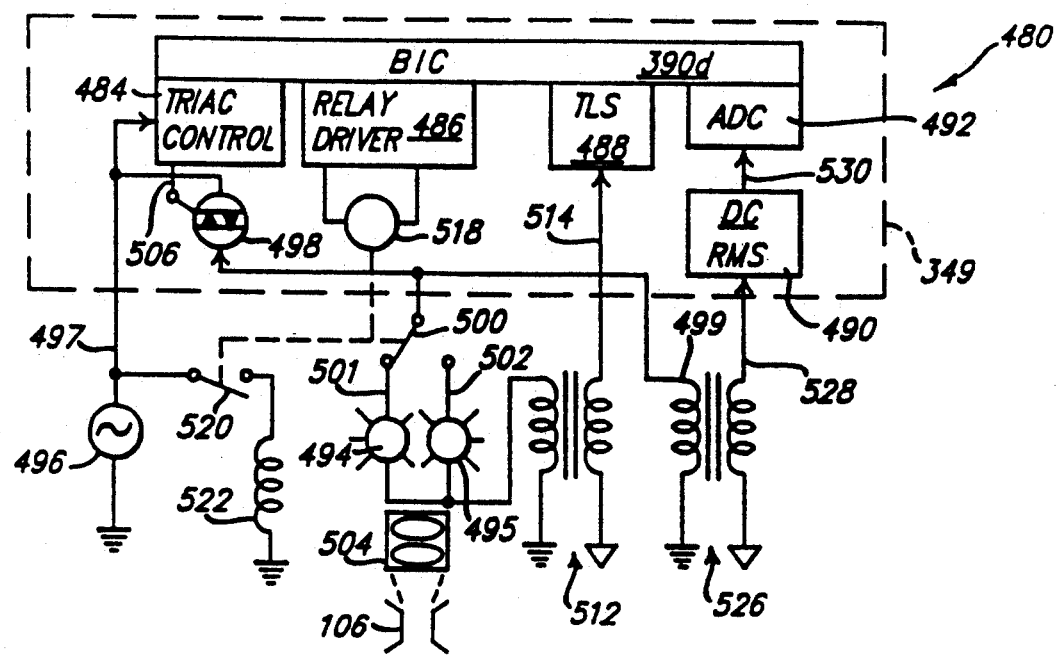
FIG. 4D is a detailed block diagram of the illumination lamp control circuitry and electrical hardware associated therewith.

FIG. 4D shows a block diagram of the fiberoptic illumination (FOI) lamp control circuit, which includes the lamp control board 449 shown in FIG. 4A, and the electrical hardware 480 controlled by PC board 349. The board 349 includes a triac controller 484, a relay driver circuit 486, a threshold level sensing (TLS) circuit 488 an RMS-to-DC converter 490 and 8-bit resolution analog-to-digital converter (ADC) 492. Conventional optoisolators are used in circuits 484 and 486 to help prevent electrical noise for these two circuits from being passed to other parts of the electronic control system 320.

The lamp drawer 41 (see FIG. 1A) includes two lamps 494 and 495 shown in FIG. 4D which are powered by a low voltage (15 volts RMS) AC signal source 496 which has its power delivered via conductor 497 to triac 498, conductor 499, Form-C relay contact 500 and then to conductor 501 or 502. During normal operation, the primary bulb 494 is employed to illuminate through a conventional focusing lens 504 receptacle 106 of front panel 90. Processor 324 provides signals via VME bus 340 to the lamp control board 449 instructing triac controller 484 as to how brightly to turn on the light bulbs 494 or 495. This is accomplished in conventional manner by the timing of the gate signal on line 506 applied to triac 498.

Isolation transformer 512 is used to monitor the light bulb current to determine if the lamp circuit is operating properly. Current passing through either bulb 494 or 495 also passes through the primary of transformer 512, causing a voltage to be developed across its secondary which is delivered by conductor 514 to TLS circuit 488, which produces an output when the sense current exceeds a predetermined threshold level. Processor 324 periodically checks to see if the output of TLS circuit 488 is on, which indicates that the bulb circuit is operating satisfactorily. If this signal should be absent, relay driver 486 energizes relay coil 518 which transfers the Form-C contact 500 so that power from triac 498 is delivered via conductor 502 to the second light bulb 495. In this manner, lamp driver circuit 480 automatically switches to the secondary lamp source 495 when the primary bulb 494 fails to operate for any reason. At the same time, electrical contact 520 closes and rotation solenoid 522 causes a mirror (not shown) to rotate into position so that light from secondary bulb 495 shines directly into focusing lens 504.

Isolation transformer 526 monitors the voltage on line 499, which is equal to the voltage applied across the light bulb. This voltage signal induces a corresponding current in conductor 528 connected to RMS/DC converter 490 which produces a DC signal on line 530 proportional to the amplitude of the signal on line 528. ADC 492 converts this into a digital value which is transferred via BIC 390d and VME bus 340 to processor 324. Processor 324 periodically examines this value to determine whether fluctuations in the applied voltage level of the bulb are occurring. If they are, processor 324 issues appropriate compensating commands to triac controller 484, thus keeping the effective power applied to the light bulbs constant, to help ensure a constant level of illumination in accordance with the illumination level setting selected by a user via keys 52.

E. Electrical Circuit For Pneumatics System (FIG. 4E)

1. Pneumatics Control Circuit

Figure 4E:
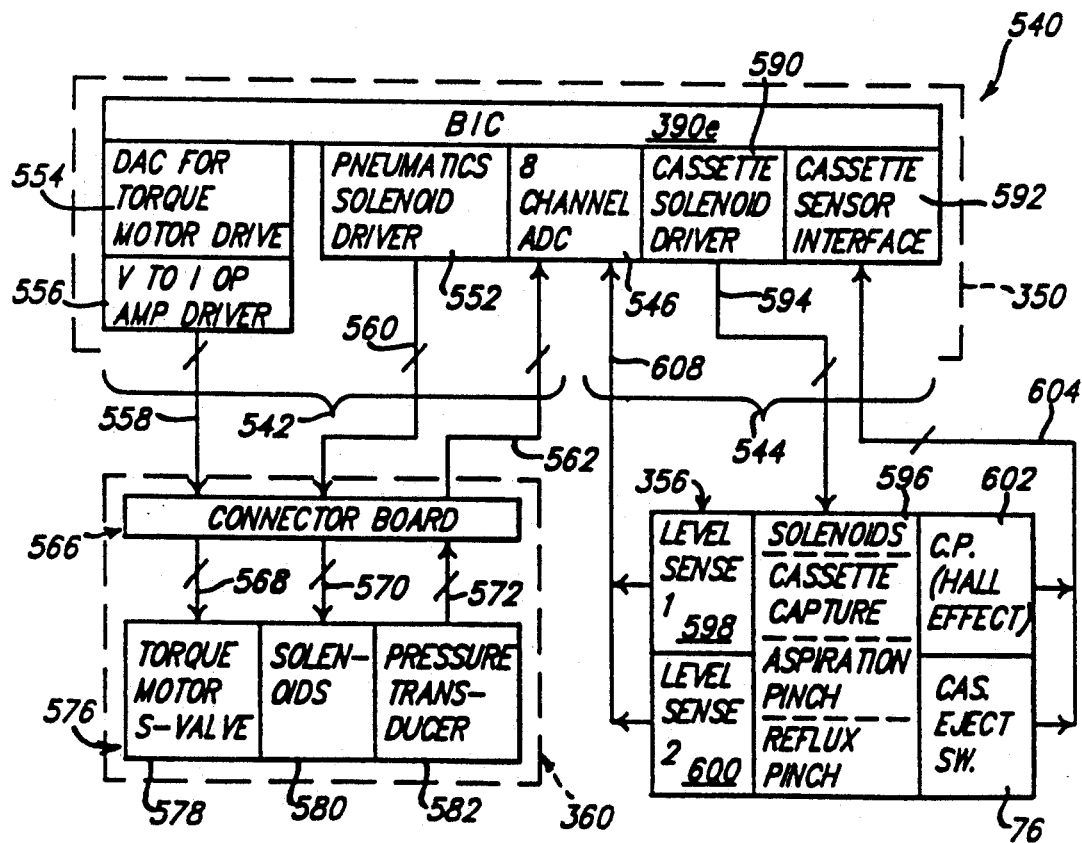
FIG. 4E is a detailed block diagram of the pneumatics control and cassette control circuitry and related electrical equipment found in the pneumatic system and cassette system of the FIG. 1 console.

FIG. 4E is a block diagram of the electrical control circuitry 540 found on pneumatic control board 350, which as shown in FIG. 4A is used to drive the electrical devices forming part of the cassette hardware 356 and the pneumatic hardware 360. The circuitry 540 includes a pneumatic control section 542 and a cassette control section 544. The BIC 390e and an 8-channel ADC 546 are common to both sections. Pneumatic control section 542 include a solenoid driver circuit 552 and a DAC 554 and a voltage-to-current op amp driver circuit 556. Three sets of conductors 558, 560 and 562 deliver signals from section 542 to a common connector board 566 located at the pneumatics drawer 44. Connector board 566 serves as a convenient termination point for three sets 568, 570 and 572 of internal conductors which run between connector board 566 and the actual electrical devices 576 being driven or read. The devices 576 include a torque motor servo valve 578 and set 580 of solenoids which operate valves and a set 582 of pressure transducers. The torque motor servo valve 578 is used to provide a proportionally metered flow of pressurized air which is used to create a desired level of vacuum for aspiration or of air pressure for operating microscissors. The rate of air flow is proportional to the opening in the valve, which is proportional to the electric current supplied to the torque motor valve 578. Processor controls this current level by sending appropriate control signals over VME bus 340 to the BIC 390e in board 540 which causes DAC 545 to generate a specified voltage level. This voltage level is converted by op amp driver 556 into an amplified current signal passed along conductors 558 and 568 to servo valve 578. Processor 324 also controls the operation of solenoid valves in the pneumatic system 44 by sending appropriate signals to BIC 390e shown in FIG. 4E, which turns on individual driver circuits, as desired in solenoid driver's circuitry 552. Thus suitable voltage signals (such as 12 volts DC) are applied along individual ones of conductors 560 and 570 to turn on desired ones of the solenoids 580.

Pressure transducers 582 generate low voltage analog signals which are routed up through conductors 572 and 562 to respective individual channels of ADC 546, which read the analog signal levels. Processor 324 polls ADC 546 periodically through BIC 390e to obtain digital values of the pressures sensed by transducers 582. Further details about the construction and operation of the pneumatics hardware 360 and operation of the pneumatic system are provided in aforementioned application Ser. No. 07/428,239.

2. Cassette Control Circuit

Cassette control section 544 includes conventional solenoid driver circuitry 590 and sensor interface circuitry 592. Solenoid drive circuit 590 provides amplified voltage signals to three solenoids used to operate two-position, three-way pneumatic valves that individually control three small pneumatic cylinders used for cassette capture, aspiration pinch and reflex pinch operations. The cassette hardware 356 includes two level sensing devices 598 and 600 which detect when fluid in the collection cassette 72 has reached predetermined levels one and two corresponding to "cassette nearly full" and "cassette full" fluid levels. Hardware 356 also includes a Hall effect switch 602 (used to detect the presence of the spring-loaded mechanical lever which is pressed when the collection cassette 72 is fully inserted in slot 70) and the cassette eject switch 76 shown on panel 190 in FIG. 1A. Sensor interface 592 reads the electrical signals on conductor 604 to determine the states of devices 602 and 76. Two channels of ADC 546 read the states of level sensing devices 598 and 600 over conductors 608. Periodically, processor 324 interrogates sensor interface 592 and ADC 546 to determine the status of sensing devices 598, 600, 602 and 76. The level sensing device 598 preferably consists of a LED and phototransistor positioned on opposite sides of the cassette 72. As the liquid level rises, a plastic ball which floats rises as well and breaks the light beam between the LED and phototransistor. The level sensing device 600 preferably consists of the same type of LED/phototransistor arrangement, but located at a slightly higher level. Further details about the cassette hardware 356 is provided in aforementioned application Ser. No. 07/428,216, now abandoned.

F. Expansion I/O Board Circuit (FIG. 4F)

1. Introduction

Figure 4F:
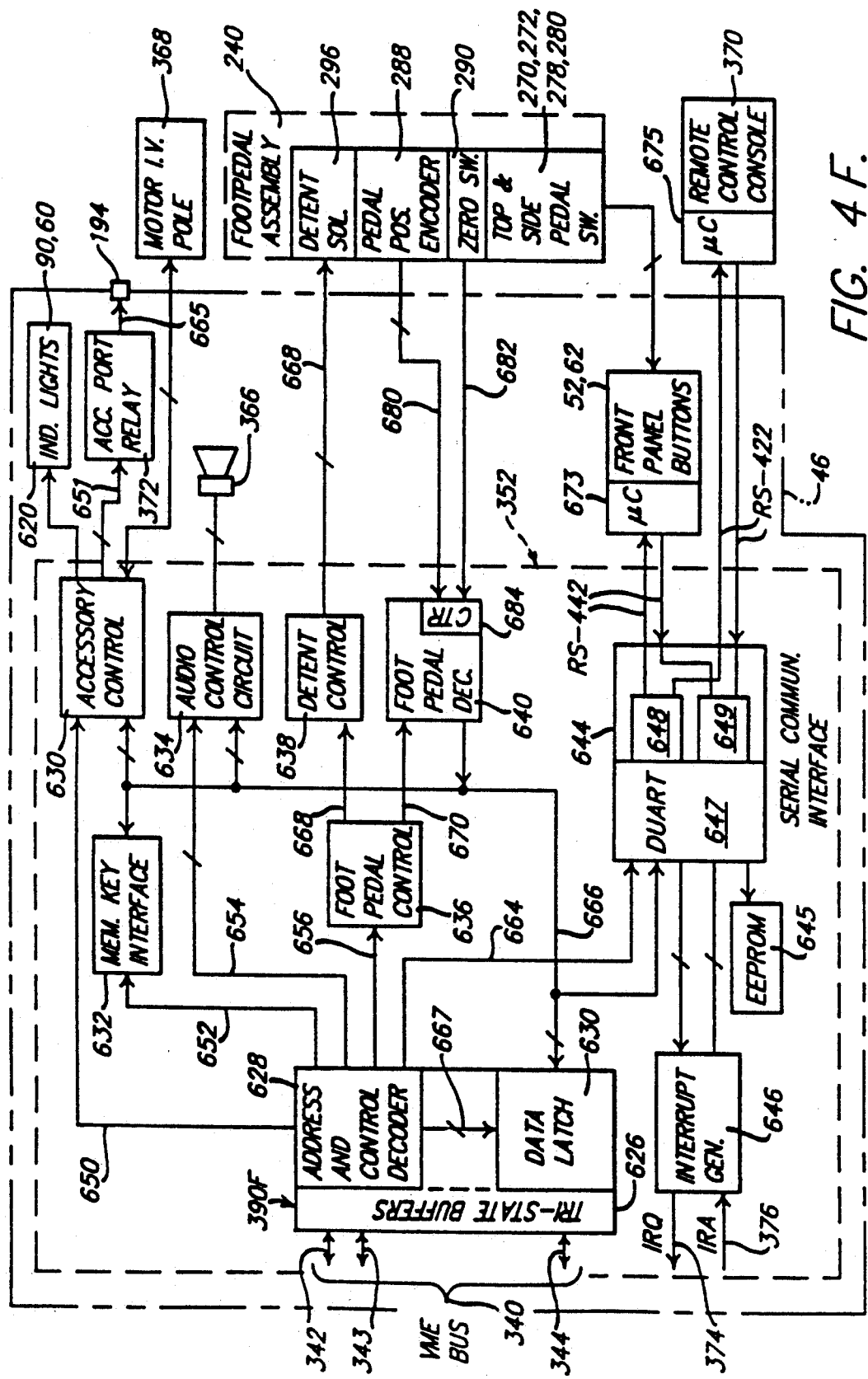
FIG. 4F is a detailed block diagram of the I/O expansion board shown in FIG. 4A and the electrical equipment interfaced therewith, which includes the remote console of the present invention.
Figure 5:
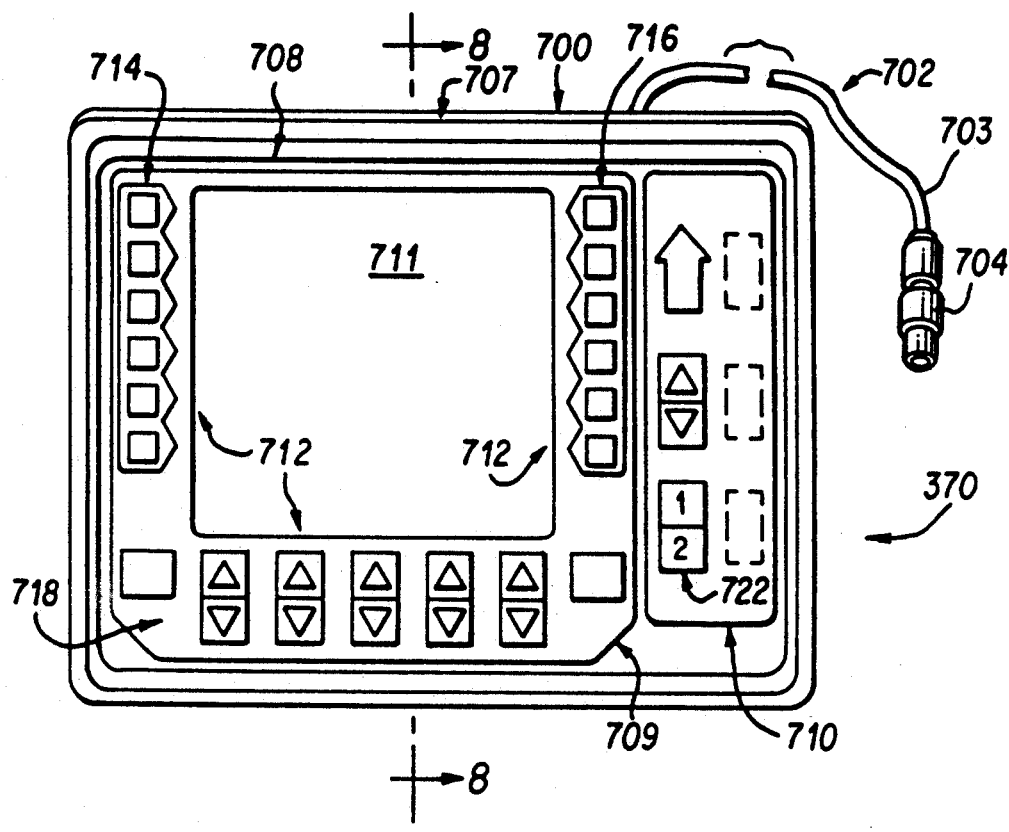
FIG. 5 is a plan view of the assembled remote control console of the present invention showing the primary front panel which has a rectangular visual display area with membrane positions positioned thereabout and a secondary display/switch panel to the right thereof.

FIG. 4F shows a detailed block diagram of the I/O expansion board 352 and the devices which it drives or reads, namely: the indicator lights on secondary front panel 60 and on connector panel 90 (represented by block 620) and relay 372 for accessory connector 194, the speaker 366, and the primary and secondary front panel buttons 52 and 62, all of which are located in or on the control console 46 (indicated by these devices being to the left of the dashed line 46, which represents the perimeter of control console 46). The board 352 also drives and/or reads devices in the motorized IV pole assembly 368, the footpedal assembly 240, and the optional remote control console 370, which are all outside of the control enclosure 46.

The I/O board 352 communicates with the VME bus 340 through a VME interface 390f which includes tri-state buffer circuits 626, address and control decoder circuit 628 and 16-bit data latch or register 630. The I/O circuitry on board 352 also includes four primary control interface circuits, namely accessory control 630, memory key control 632 for memory key 132, audio control 634 for speaker 366, and footpedal control 636. Control circuit 636 in turn directs the operation of two slave circuits, namely detent control 638 and footpedal decoder 640 which actually communicate with devices in footpedal assembly 240. Board 352 also includes a conventional serial communications interface circuit 644 which drives and reads in conventional fashion an interrupt generator circuit 646 and a non-volatile memory 645, which preferably is an electrically erasable programmable read only memory (EEPROM). Circuit 644 includes three conventional integrated circuit (IC) chips, namely a dual universal asynchronous receiver/-transmitter (DUART) 647, a dual-channel RS-422 transmitter chip 648, and a dual-channel RS-422 receiver chip 649, all functionally connected as shown in FIG. 4F.

The primary interface circuits 630-638 and the serial communications interface 644 communicate with VME bus interface 390f via control signals passed along dedicated control lines 650-656 and 664. Data to be sent to and/or received from circuits 630-638 or communications interface 644 is passed along an internal 16-line data bus 666 connected to data latch 630. Footpedal control 636 communicates with slave circuits 638 and 640 via lines 668 and 670. Each of the primary control circuits and the communications interface 644 contains a data latch circuit for receiving, holding and/or transmitting data to internal data bus 666.

Address and control decoder 628, upon receipt of commands from processor 324 via VME bus 340, decodes the command and address signals on lines 342 and 343, and in accordance with the decoded instructions distributes the desired control signals and/or via lines 667 commands data signals to the control interface circuit 630–636 or 644 which the processor 324 desires to address. The control interface circuits 630-636 have no intelligence and do not on their own seek to communicate with processor 324. Instead, processor 324 just periodically writes or reads data to these control circuits.

2. Functions of Serial Communications Interface 644

The communications interface 644 has two devices connected to it which have intelligence, namely microcontroller 673 associated with the two front panels 48 and 60 on console 46 and microcontroller 675 associated with optional remote controller 370. Serial communications interface 644 converses with the microcontrollers 673 and 675 using the well-known RS-422 communications protocol at a suitable data rate, such as 9600 baud. Whenever either of these two microcontrollers has information to be sent to processor 324, it serially sends a byte of information to the communications interface 644 which in turn automatically causes an interrupt to be generated. Communications interface 644 is identified as the source of the interrupt, the interrupt is acknowledged via line 376, and the processor 324 causes data serially communicated to the DUART 647 by the microcontroller to be loaded into the data latch 630, and then via VME bus 340 reads the data from latch 630 in one of its next I/O cycles. Microcontroller 673 has its own internal oscillator and micro program. It continuously monitors all of the buttons 52 and 62 found on front panels 48 and 60 of the control console 46 to determine whether they have been depressed. The buttons are electrically arranged in a matrix of row and columns, and by interrogating each position of the matrix the state of all the buttons is determined. The microcontroller advises the processor whenever a button is pressed, and keeps periodically advising the processor 324 of this fact for as long as the button remains pressed. Microcontroller 673 also monitors, as part of the aforementioned matrix of buttons, the status top buttons 270 and 72 and side pedals switches 278 and 280 within the footpedal assembly.

The microcontrollers 673 and 675 are provided in order to ensure that the main processor 324 is apprised of changes in status at the front panel console or remote control console virtually immediately for a very quick response to operator requests. In other words, all the routine functions which need not be performed quickly by the main processor 324 are made to wait while processor 324 responds to an interrupt and reads the data from the microcontroller and puts it into a table in main memory 325 one byte at a time. In main memory, a table listing the states of all the buttons on the main console and the remote control console is kept. The microcontrollers 673 and 675 only advise the main processor 324 of changes in the state of any of the buttons. In this manner, communications between the microcontrollers 673 and 675 are handled far more efficiently than updating the entire table each time an interrupt is generated.

Microcontroller 675 operates in the same manner as microcontroller with respect to the matrix of buttons it monitors. The remote control console 370 also contains a keyboard interface circuit almost identical to interface circuit 680. This interface circuit is described in detail below.

Communications interface 644 also reads and writes data to EEPROM 645 in conventional fashion. EEPROM 645 is provided so console 46 can store, in a non-volatile manner, any user-programmed default values, configuration codes, calibration data and/or any other pertinent parameters which may be entered in by the user.

3. Accessory Control Circuit 630

The accessory control 630 contains: a plurality of memory latches and indicator light driver circuits dedicated to driving the indicator lights 620 on connector panel 90 and secondary panel 60; a plurality of memory latches, relay driver circuits, sensing circuits and an optical position decoder, all of which are dedicated to sending control signals to and receiving information from motorized IV pole hardware 368; and a latch and relay driver for operating relay 372. When a relay driving signal is applied to line 662, relay coil 372 is energized, which closes a normally open contact and thus completes the circuit available on lines 664 connected to the connector receptacle 194 shown in FIG. 1B. The details of the electrical devices and circuits in the motorized IV pole 368 are described in application Ser. No. 07/428,166, now abandoned, entitled "Motorized IV Pole Assembly," and thus need not be described here.

4. Audio Control Circuit 634

The audio control circuit 634 is of standard design, and uses a conventional programmable sound generation circuit on a large scale integration (LSI) chip to produce the various tones at various amplitudes used to indicate device operation and provide audio error signals to the console user. The output signal from this chip drives a separate conventional low-power audio amplifier chip, whose output is connected to and drives speaker 366. A suitable sound generator is available from Microchip Technology, Inc. of Chandler, Arizona as Model No. AY8930. One of the unique features provided by control console 46 is the user of select various tones and amplitudes for the selected tones to represent different conditions or states that the control system 40 may be placed in by the surgeon. A further description of this aspect of the control system 40 is provided in aforementioned application Ser. No. 07/428,232, now abandoned) entitled "Control System For Ophthalmic Surgical Instruments."

5. Footpedal Control Circuits 636–640

In accordance with commands from footpedal control 636, the detent control 638 provides positive and negative 24 volt DC power signals on lines 668 to operate the detent solenoid 698. A momentary +24 VDC signal extends the armature of solenoid 698 while a momentary −24 VDC signal causes it to retract. Conventional magnetic and/or mechanical detents built into solenoid 698 hold its armature in the last position the signals on lines 668 placed it in.

Footpedal decoder 640 receives low-voltage quadrature signals over conductors 680 from encoder 288, and a low-voltage digital signal on line 682 from zero switch 290. Switch 290 is released whenever footpedal 250 is moved more than two degrees from its spring-returned position, that is, the position pedal 250 is in when it is not pressed at all. When the signal on line 682 is in its reset state, bidirectional multiple stage digital counter 684 within decoder circuit 640 is held in a reset state. As soon as signal 682 goes to its opposite state, counter 684 is allowed to operate under the control of the quadrature signals on lines 680 which increment or decrement the counter with each pulse. Thus the accumulated count in counter 684 reflects the true angular position of footpedal 250. Processor 324 periodically (once every 50 milliseconds) reads the value in counter 684 by sending appropriate control signals to bus interface 390f so that counter 684 can send its present count to data bus 666, where it is held by latch 630 until read by the processor 324 via VME bus 340.

The status of top button switches 270 and 272 and the side pedal proximity switches 278 and 280 of the footpedal assembly 240 are also read through microcontroller 673, which as previously explained serially transmits information to communications interface 644, through internal bus 666, bus interface 390f and VME bus 340 to processor 324.

V. The Remote Control Console (FIGS. 5–14)

A. Hardware Of Remote Console 370 (FIGS. 5–8)

The remote control console 370 of the present invention which is also from time to time referred to as the remote control unit or remote controller is illustrated in, and will be fully described in conjunction with, FIGS. 5–14. The remote controller 370 is constructed in its own molded plastic housing 700 and is connected by an electrical umbilical cord or cable assembly 702 including multiple-conductor cable 703 and 8-pin connector 704 to the mating connector 706 provided on the plate 136 of the front of main control console 46 shown in FIGS. 1 and 2. The remote console 370 has a slightly downwardly-sloping front surface 707 with a membrane switch assembly 708 shown in enlarged view in FIGS. 9 and 10. This assembly 708 includes a large rectangular primary panel 709 and a smaller rectangular secondary panel 710 to the right thereof. On the primary panel 709 is a transparent visual display area 711, a plurality of pushbuttons or touch sensitive switches 712 organized in two groups 714 and 716 along the left and right sides of the display area 711, and a third group 718 along the bottom of the display area 711. The secondary panel 710 located to the right of the primary panel 709 has additional pushbuttons or switches 722 arranged in a column.

The remote control console 370 is controlled by a microcontroller 675 within the housing 700 and is capable of providing several different illuminated messages or legends in a manner that will be described shortly.

Figure 6:
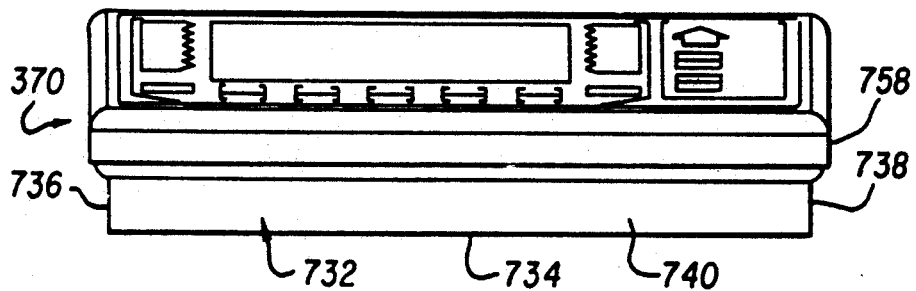
FIG. 6 is front view of the FIG. 5 remote controller.

FIGS. 6 and 7 are front and right side views of the remote console 370 showing a presently preferred shape for housing 700. The console 370 is intended to be placed on a flat (or slightly inclined) surface such as indicated by dotted lines 730 in FIG. 7. The housing 700 has a rectangular bottom 734, trapezoidally-shaped left and right side wall portions 736 and 738, rectangularly-shaped front and rear wall portions 740 and 742 with the cable 703 extending from the rear wall 742. The housing 700 also has a upper section 744 with rounded upper and lower edges 746 and 748 extending from elongated rectangular front and rear surfaces 750 and 752 and left and right side surfaces 756 and 758.

Figure 11:
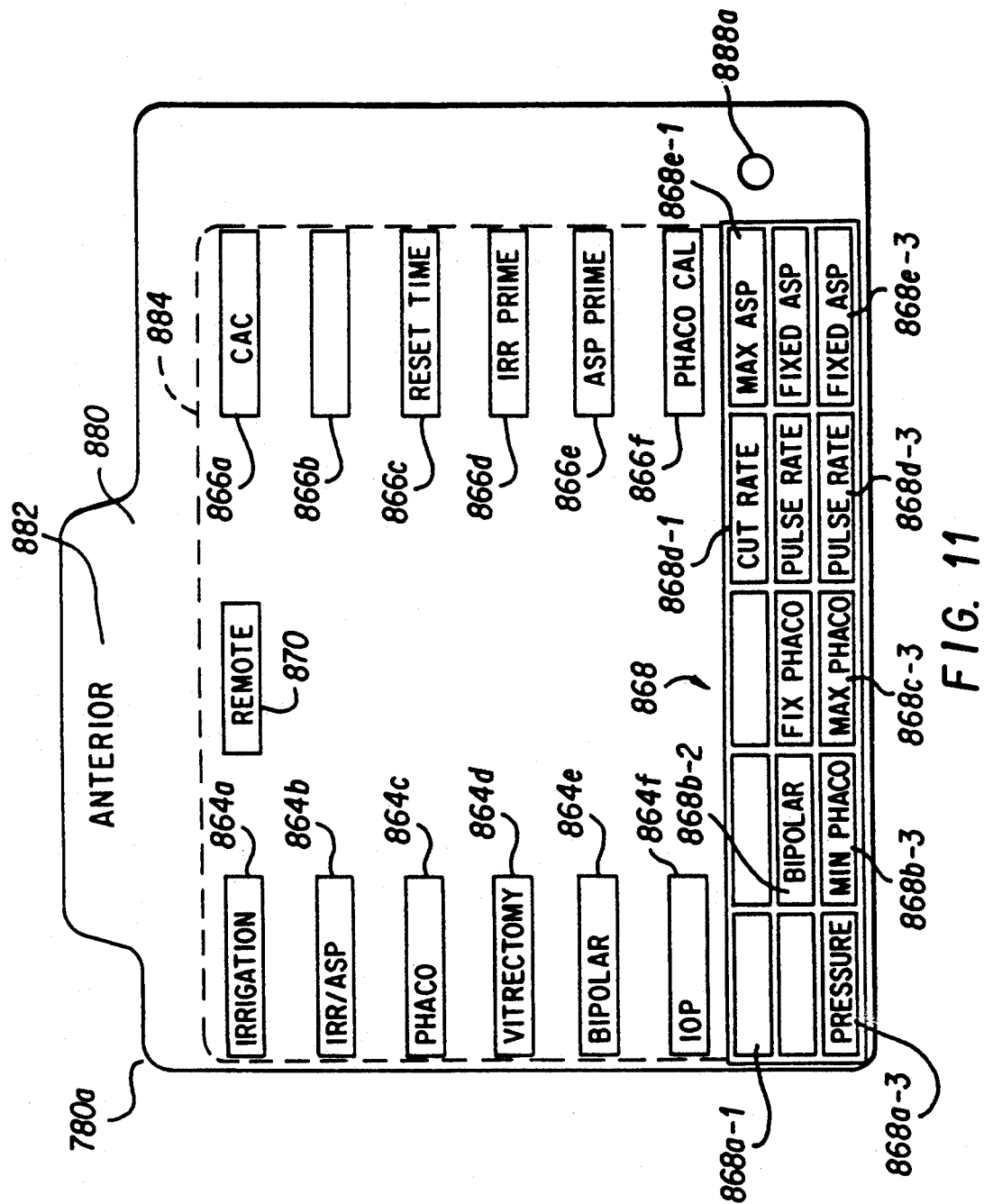
FIG. 11 is a first legend card or mask designed for installation into the FIG. 5 remote console which includes a first set of English-language legends at predetermined locations within the visual display area indicated in dotted lines.
Figure 12:
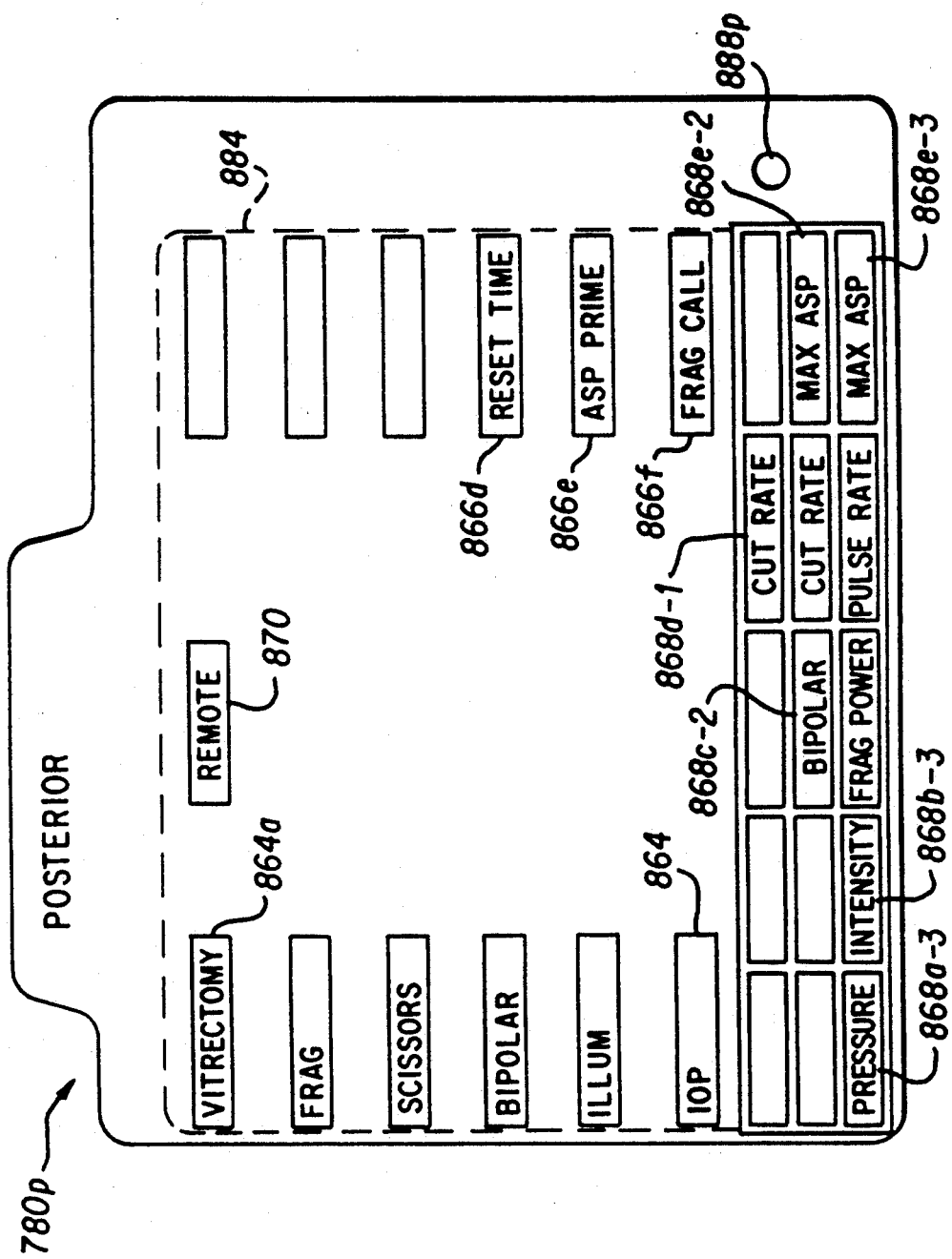
FIG. 12 is a second card or mask for use with the FIG. 5 console which has a different set of English-language legends in predetermined locations within the display area indicated in dotted lines.

FIG. 8 shows that the base and upper sections 732 and 744 of housing 700 may be injection-molded together as one piece if desired. The housing 700 preferably includes an inner chamber 760 having a lower section 762 and an upper section 764. A cord 703 is routed into the lower section 762 where a connector 766 on the end thereof is received by a mating connector 768 so that electronic signals may be passed between the microcontroller 675 and main processor 324. The upper chamber 764 of housing 700 contains a printed circuit (PC) board 770 resting on shoulders 772 and 774, and membrane switch assembly 708 which fits snugly into the upper chamber 764 where it abuts side surfaces 776 and 778. A removable card 780 bearing multiple legends, which will be more fully described with respect to FIGS. 11 and 12, is inserted into a slot 782 near the top of rim section 744 of the housing 700 until it meets the bottom surface 788 near front wall 750 of the housing. Slot 782 leads to a small very thin sheet-like cavity 784 which is sandwiched between upper and lower portions of the membrane assembly 708.

PC board 770 contains all of the electronic components which will later be described with respect to FIG. 14 except for those contained as part of the membrane switch assembly 708. Included among the components it is a group 790 of back illumination lights 792, which may be mounted into standard PC board sockets 794 shown therebelow.

The bottom 734 of housing 700 includes a metal cover plate 796 which, along with interior housing surface 798 and wall 800, forms an elongated chamber 802 where one or more legend cards 780 may be stored when not in use in chamber 784. Near the entrance of 804 of the chamber 802 may be provided a leaf spring 806 to help retain the cards in the chamber.

B. Membrane Switch Assembly Chamber (FIGS. 9-10)

FIGS. 9 and 10 illustrate the geometry of interior chamber 784 in assembly 708 for the removable legend card 780 much more clearly. The outline of pocket 784 is indicated by left and right vertical hidden lines 814 and 816 and horizontal hidden line 818. The upper part of the chamber 820 is open and leads to slot 782 shown in FIG. 8.

FIG. 10 shows that membrane switch assembly 708 is preferably a five layer sandwich. The first or top layer is a protective liquid-resistant plastic skin 830 which covers the membrane switches 712 and has a transparent window fit therein in display area 711. The second layer (not shown) is a metallized polymer material providing an electrostatic protection layer between the top layer 830 and the membrane switch board 832. This layer covers the entire display panel exclusive of display area 711. This foil layer is earth grounded internally in the lower chamber 760 by the cable shield of item 703. The third layer is a membrane switch board 832 constructed in a conventional manner of a dielectric board material having conductive metal row and column traces provided thereon for matrix addressing of the membrane switches and the usual mechanical spring material to bias each individual membrane switch into a normally open position or state so that pressure must be applied to the switch in order to make it assume its normally closed position or state. Layer 832 is a void in the display area 711. The fourth layer of the assembly 707 is a spacer layer with the left and right portions 834 and 836 forming the side boundaries of card chamber 784 and the bottom portion 838 forming about the bottom boundary 818 of card chamber 784. The fifth or bottom layer 840 of the assembly sandwich is a conventional high-strength dielectric material which provides rigidity so that the assembly may be supported by four bolts 841-844 which are passed into thru-holes in the base section 732 of the housing 700 where they are tightened down with suitable fastening means such as nuts which hold the membrane switch assembly 707 securely to the housing.

C. The Legend Fields In Display Area 711 (FIGS. 9. 11-13)

The operation of the display area 711 in combination with the buttons or switches 712-722 may be best understood by looking at FIGS. 9 and 11-13 together. The display area 711 is shown there as being conceptually divided into a central field region 862 (which is not used in the preferred embodiment but could be used if desired), a left side display region 864, right side display region 866, bottom display region 868 and a top display region 870. The side regions 864 and 866 each consist of six horizontal fields stacked one above the other and positioned to correspond to the locations of the buttons of button groups 714 and 716. By virtue of the adjacent location of the top button of the button group 714 and the top field of the region 864, for example, a message in the upper left hand corner of the display area 711, i.e., in this top field 864a, is readily understood by the operator or user as referring to the upper leftmost button 714a. The other buttons in fields are similarly paired. This arrangement allows the indicated function of each of the buttons 714 or 716 to be readily changed by simply just changing the legend displayed in its adjacent field. In a similar manner, each pair of buttons (such as buttons 718a-1 and 718a-2) is associated with one of the three-part fields along the bottom region (such as region 868a). In general, the upper row of buttons, i.e., buttons 868a-1 through 868e-1, are used to increment a setting or parameter of the type displayed in the corresponding fields 868a-868e of display area 711 directly above, while the buttons in the lower row, i.e., buttons 868a-2 through 868e-2, are used to decrement the displayed type of settings or parameters.

The use of the display area 711, in combination with legend cards such as card 780, which has fields that can be labeled any way desired, permits the legend for the buttons to be in almost any language. Button 718f is used to bring up an information screen on the display 50 of the main console (but not the remote console) to assist the operator, such as by further explaining functions associated with choices on the display menu (which, as will be explained shortly, may be either on the display 50 of the main console, or on the display area 711 of the remote console 370). Button 718g is used to return to an earlier menu screen in a chain of related menus or other screens.

The fields 864-870 shown as dotted rectangles in FIG. 9 represent the back-illumination lights mounted on PC board 770 which can be turned on and off via the microcontroller 375 operating in response to command signals received from the main processor 324. For convenience, the lights will be designated by adding the suffix "L" to the reference numerals used to describe the corresponding fields, when it is desirable for sake of clarity to distinguish between the field in a positional sense and the back- illumination device as a source of light.

The functions of the secondary panel 710 on the remote console 370 are similar to those of the secondary panel 60 found on the main console 46, and will now be described. As best in FIG. 9, secondary panel 710 is used to control a motorized IV pole (not shown) that supports one or more bottles or pouches of balanced salt solution used to provide irrigation during ophthalmic surgical procedures. As previously described in Section I.A. 4 above, the motorized IV pole includes a reversible electric motor/gear reducer combination which adjusts the height of the IV pole up or down as desired. The particular height may be selected via the buttons on the main control panel 60, or those on panel 710 of the remote control. Buttons 722a and 722b are used respectively to lower and raise the pole incrementally, as long as the button is held. Button 722c, is used, under emergency conditions, to send the pole upward rapidly at roughly twice the speed of button 722a as long as the button is held. Buttons 722f and 722g are used respectively to change the height for the IV pole either to a first or second preset level. Indicator emblems 724c, 724f and 724g are illuminated when the IV pole function is operative, indicating buttons 722a, 722b, 722c, 722f and 722g are active. The 20 operation of these functions and the construction of the "Motorized IV Pole Assembly" is described in aforementioned application Ser. No. 07/428,166, now abandoned, of the same title.

D. Legend Cards & Associated Functions

FIG. 11 shows a legend card 780a with one possible group of legends thereon, while FIG. 12 shows another legend card 780p with another group of possible legends thereon. While these legends are in the English language, those skilled in the art will appreciate that the legends may be in a foreign language or universal symbols which would be readily recognized independent of the language of the user. The card 780a shown in FIG. 11 represents a most of the legends which are displayed upon the display screen 50 of the main console 46 when various anterior segments surgical procedures are performed. Similarly, the legend card 780p contains a number of different legends which are related to various surgical procedures which are performed during posterior segments operations. As previously described in Section II.A of this specification, the microsurgical system 40 is capable of up to 9 (or more) modes. A number of the legends on legend card 780a or 780p may be readily understood by referring to this previous discussion. For example, the legend 864a is illuminated when the irrigation mode is selected, the legend 864b is illuminated when the irrigation/aspiration mode is selected, the legend 864c is illuminated when the phaco mode is selected, legend 864d is illuminated when the vitrectomy mode is selected, legend 864e is illuminated when the bipolar mode is selected, and legend 864f is illuminated when the IOP mode is selected. Legend field 866 is illuminated when the CAC mode is selected. Legend field 866 is presently unassigned and is available for any additional mode which may be made part of the anterior segment operations capability of the control console 46. The legend field 870 is illuminated whenever the remote control console 370 is connected to the main console 46 and in communication with the main processor 324 and ready for use by a surgeon or other user.

The legend "RESET TIME" in field 866c (or in FIG. 11 field 866d) is illuminated whenever the system 40 is in phaco mode or fragmentation mode. Both phaco mode and fragmentation mode involve the use of ultrasonic power produced by the phaco control circuit 430 shown in FIG. 4C. In phacoemulsification procedures, irrigation is provided through the handpiece whereas in the fragmentation (frag) procedures, irrigation is normally provided through a cannula placed in a separate incision in the posterior segment of the eye. In either the phaco mode or frag mode, the microprocessor 324 keeps track of the total elapsed time the ultrasonic power has been in use. The button 716c "RESET TIME" field 866c when pushed, resets the register in which the accumulated time is held to zero. The illumination of the legend 866c informs the user of the remote console that the button 716c is to be used for this purpose.

In FIG. 11, the legend 866d stands for "irrigation prime." The legend in field 866e stands for "aspiration prime" in FIG. 11 and in FIG. 12. When these fields are illuminated, it means that the adjacent buttons, i.e., button 716d and 716e may be used for the purposes indicated in the adjacent fields. When irrigation mode, irrigation/aspiration mode, or vitrectomy mode is selected, the field 866d will light up, so that the user can prime the probe or handpiece to be used. Once the button 716d is pushed, this selects the irrigation prime function and the field 866d begins to blink, and the "aspiration prime" field 866e is now fully backlit to indicate to the user that the aspiration tubing should be primed. When the corresponding button 716e is selected, the aspiration prime field 866e begins to blink. When the member of the surgical team has completed the irrigation and/or aspiration priming functions, he or she presses the corresponding button to deactivate the corresponding function that is blinking, and the backlighting for that field is turned on continuous to indicate that the function is no longer active.

The legend 866f in FIG. 11 and in FIG. 12 is only illuminated when the phaco mode (or fragmentation mode) is selected. This informs the user that the adjacent button 716f when pressed will invoke the named calibration procedure, which is described in detail in aforementioned patent application Ser. No. 07/428,232, now abandoned entitled "Control System for Calibrating and Driving Ultrasonic Transducer."

The group 868 of illuminatable fields 868a-1 through 868e-3 are arranged in a three row by five column layout, and are used in order to identify the functions associated with corresponding pairs of buttons 718a through 718e positioned below corresponding columns of legend fields 868a through 868e. Normally, a legend field is not illuminated. The typical incidences during which such legend fields are illuminated will now be described. Referring now to FIG. 11, the fields shown on anterior legend card 780a which is used when performing various anterior surgical procedures are as follows: In first column 868a, the "pressure" field 868a-3 is illuminated only when in IOP mode. Thus the pair 718A of buttons below may be used to increase or decrease this output pressure produced at the IOP connector 150 shown in FIG. 1A. When in bipolar mode, the legend field 868b-2 is illuminated. When in vitrectomy mode, the legends 868d-1 and 868e-1 are illuminated, and button pairs 718d and 718e are used for adjusting the cut rate and the maximum aspiration setting respectively. In the fixed phaco mode, legend fields 868c-2, 868d-2 and 868e-2 are all illuminated and corresponding button pairs 718c, 718d and 718e are respectively used for adjusting the fixed phaco power setting, the pulse rates and the fixed aspiration setting. In the "linear phaco" mode, four legend fields are illuminated, namely fields 868b-3, 868c-3, 868d-3 and 868e-3, indicating that corresponding button pairs 718b through 718d respectively are enabled for controlling the minimum phaco power setting, the maximum phaco power setting, the phaco pulse rate and the fixed aspiration setting.

When the posterior card 780p is inserted into slot 784 of the remote console 370, the group 868 of legend fields are used in the following manner as indicated in FIG. 12. In the scissors mode, legend field 868d-1 is illuminated indicating that the pair 718d of switches may be used to adjust the cut rate of the scissors during "variable rate" cutting operation. The legend field 868a-3 is illuminated only in the IOP mode to indicate that IOP pressure may be adjusted via the button pair 718a. In the illumination mode, the legend field 868b-3 is illuminated to show that button pair 718b may be used to adjust the electrical power applied to the FOI lamp 494 or 495 (see FIG. 4D) to adjust intensity of illumination delivered via illumination probe 100. In bipolar mode, the legend field 868c-2 is illuminated indicating button pair 718c may respectively be used to adjust the bipolar power level produced via bipolar control circuitry (shown in FIG. 4). In the vitrectomy mode, legends 868d-2 and 868e-2 are illuminated indicating that button pair 718d and 718e may be used to adjust the cut rate and maximum aspiration setting. In the fragmentation mode, legend 868c-3, 868d-3 and 868e-3 are illuminated, indicating that button pairs 718c, 718d and 718e may respectively be used to adjust ultrasonic power level, pulse rate and maximum aspiration setting.

The legend card 780 is sized to fit snugly within the chamber 784 of the membrane switch assembly 707. A tab or label section 880 is provided with a suitable printed legend such as "anterior" on card 780a or "POSTERIOR" on card 780p to indicate the type of surgical operations the legends on the particular card are associated with. For convenient reference, the display region 711 of the primary panel is indicated by dashed lines 884. The legend cards are preferably made of a durable transparent plastic material and may if desired be made black (or other dark color) in all areas except those where the legends are, which should remain transparent except for the legends themselves. Alternatively, the rectangular box indicating the position of each of the fields 864a through 870 may be illuminated and only the actual legend itself within the field be provided. In the preferred embodiment of the legend cards 780 of the present invention, the entire transparent card has been covered with a gray film such as a dye or paint, and only the letters themselves have been left clear. Thus the lettering, such as the word "irrigation" in field 864a will appear illuminated while all of the surrounding areas appear dark when the back- illumination light for this field is turned on.

To ensure that the proper legend card is inserted into the remote console 370, the console 370 includes a means for checking which card is inserted into the slot 784. This means also ensures that the card has been inserted all the way into the slot, and therefore is in its proper position to facilitate alignment of back-lighting with transparent lettering card. This is accomplished by the two small transparent regions 888a and 888p respectively provided on cards 780a and 780p. Note that these two transparent circles are located in different positions. An optical transmitter/receiver system is provided for each respective region 888a and 888p. The processor 324 in the main console 46 knows which mode the user has selected by the buttons 54 or 56 which have been pressed., and therefore knows whether anterior or posterior operations are in use. Thus, when the remote controller 370 is plugged in and a card 780 inserted into it, the processor 324 can check for the presence of the proper hole by interrogating the outputs of the optical sender/receiver circuits to ensure that the proper card is present. If the wrong card is present, as indicated by the wrong hole 888 being detected, or if there is no card or the card is not inserted properly, which is indicated by both sender/receiver circuits being off or both being on, the remote console is not enabled and none of the legend fields are illuminated. Only when the proper hole 888a (or 888p) is detected, and the other transparent hole 888p (or 888a) is blocked will the "REMOTE legend field 870 be illuminated, and will the remote console 370 be allowed to affect or modify the surgical modes, procedures or functions to be performed or controlled by the control system 40.

Figure 13:
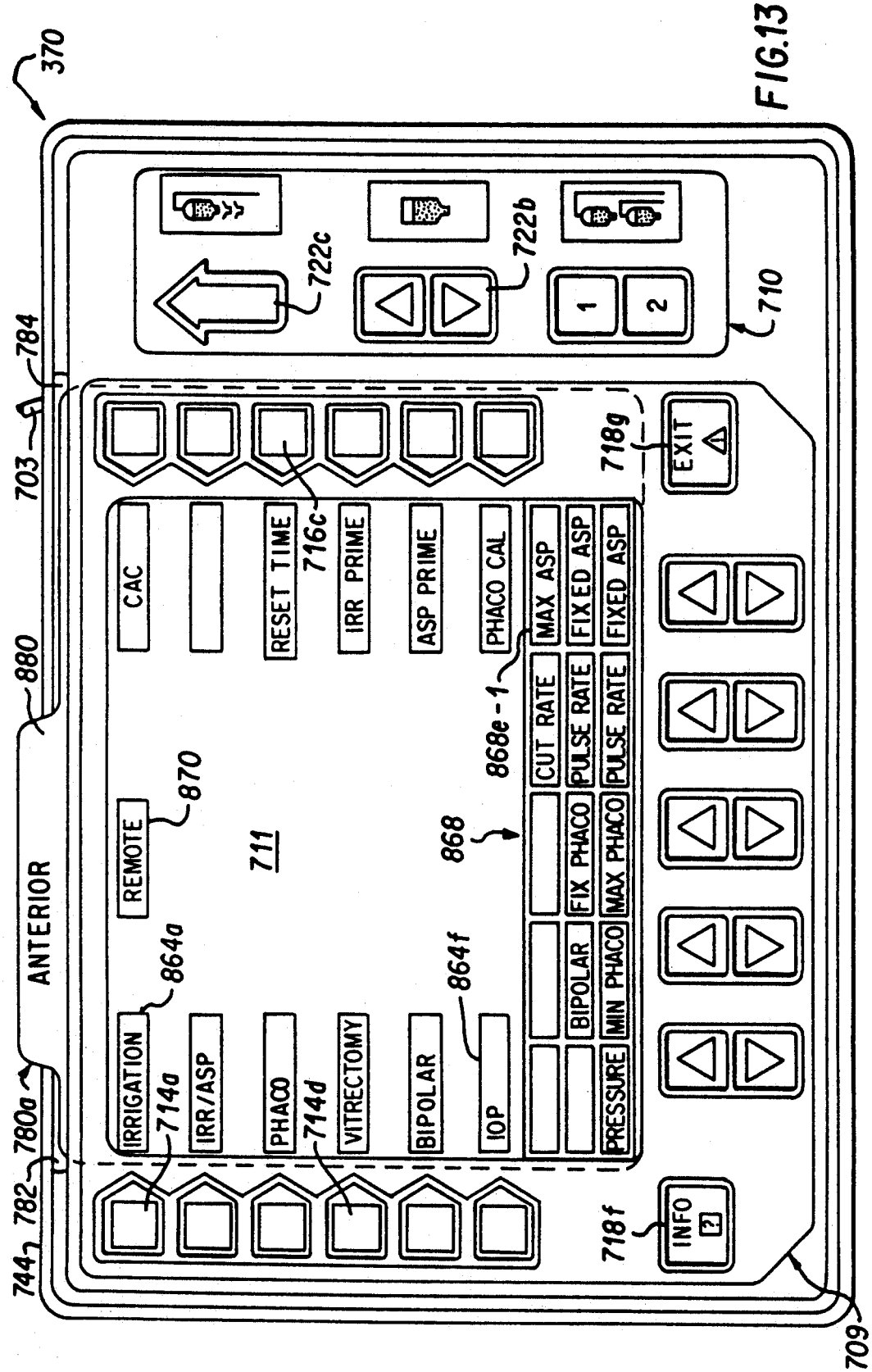
FIG. 13 is a view of the FIG. 5 console with the legend card of FIG. 11 inserted therein and with all back-illumination lights turned on so that all of the legends are visible.

FIG. 13 is a view of the remote control console 370 which has the anterior card 780a inserted therein. As may be seen, the identification tab 880 projects outside of the slot 784 so that the user may know what legend card is in the slot whether or not the controller is plugged in and powered up. For convenience, all of the legend fields 864–870 are shown in FIG. 13 as being illuminated. In practice, only those fields associated with a particular mode of operation which has been selected would be illuminated. Illumination of such fields would end when the mode was deselected. In the Storz DAISY console, the CRT display includes similar fields and legends, although there are not as many buttons in the button columns 54 and 56, and bidirectional endless digital potentiometers were provided instead of the button pairs 58 for adjusting parameters. Further details of the various surgical procedure menus provided in the DAISY console are found in aforementioned patent application Ser. No. 07/267,713, which is a continuation of application Ser. No. 06/928,170 entitled "Control System for Ophthalmic Surgical Instruments." Many of the menus of main console 46 are similar to those found in the DAISY console as well. Further information about menus for display screen 50, is found in aforementioned application Ser. No. 07/428,232 now abandoned as well.

As thus illustrated by FIG. 13, the remote control console 370 has the ability to simulate a multitude of surgical procedure screens which are displayed on the display screen 50 of main console 46. In particular, the microcontroller 675 of remote console 370, operating under the control and direction of main processor 324, can selectively illuminate any one of the desired fields. Further, the remote console 370 has the ability through the buttons 712 and 722 to provide information to change, modify and/or adjust surgical modes, the procedures to be performed, remote accessory equipment, such as the motorized IV pole, and to modify parameter settings. Further, the remote console 370 is capable of maintaining the display of a particular menu in its display area 711 while the display field 50 of the main console 46 is displaying a different menu or set-up information. Such an information screen may be requested via the information button 718f on the remote console or the corresponding button 58f forming part of the primary panel 48 on the main console 46.

E. Control Circuitry In Remote Console (FIG. 14)

Figure 14:
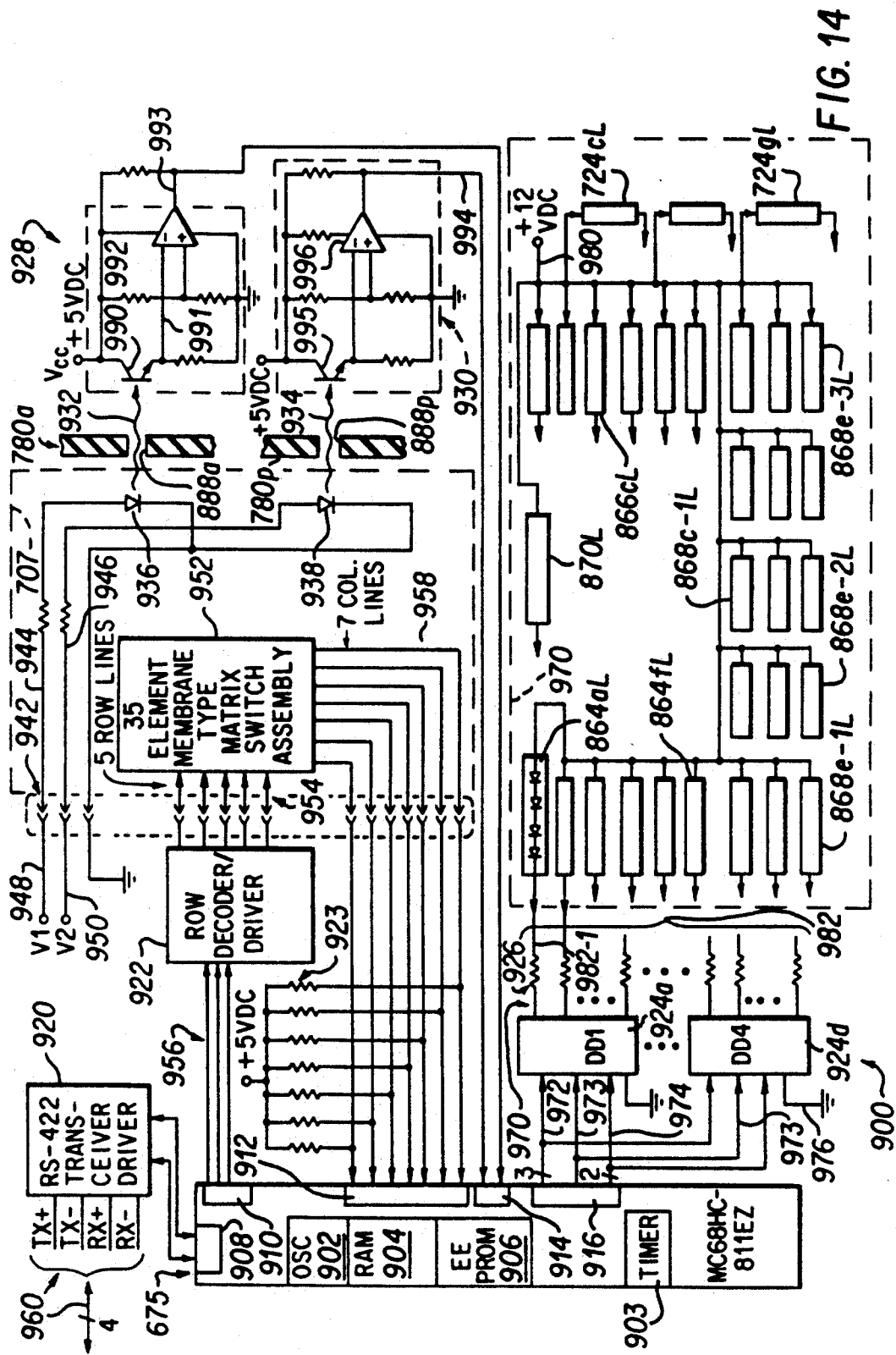
FIG. 14 is a detailed block diagram schematically showing the electronic circuitry including a microcontroller used within the FIG. 5 console.

FIG. 14 shows the electronic control circuitry 900 used in the remote console 375. The circuitry 900 is operated under the control of microcontroller 675, which has: its own internal time base 902; its own "watchdog timer" 903 (as detailed further below); its own random access memory (RAM) 904; its own non-volatile memory 906 which may be an EEPROM; a serial communications interface port 908; and various input/output (I/0) ports 910–916 whose functions will become apparent shortly. The size of memories 904 and 906 may be as needed, such as 256 bytes and 2 kilobytes, respectively. In the preferred embodiment of circuitry 675, an eight-bit microcontroller is used.

Circuitry 900 also includes an RS-422 transceiver driver 920, a 3-to-8 row decoder/driver 922, four addressable decoder/drivers 924 with at least eight bits of memory each, a bank of resistors 926, two photo-receiver circuits 928 and 930 which respectively detect optical radiation (infra-red) indicated by arrows 932 and 934 emitted by photo-diodes 936 and 938.

In FIG. 14 the components within the membrane switch assembly 707 are within the dashed lines bearing the same reference numeral. Connections to the assembly 707 are made through a 16-pin through-hole socket connector assembly 940. The male or pin portion 942 of connector assembly 940 may be seen in the lower corner of FIGS. 9 and 10 with straight pins 944 and 946 shown in FIG. 10. When the connector 940 is plugged together properly, power passes from the conductor 948 and 950 to the light emitting diodes 936 and 938. Thus, the presence of all electrical power at these diodes indicates a proper connection at connector 40. Serial communications between the main console 46 and the microcontroller 675 in the remote console are handled by conventional transceiver driver chip 920 which communicates over four conductors 960 with the serial communications interface 644 shown in FIG. 4F.

All of the buttons 712 and 722 on the remote console 370 are organized into a five row by seven column addressing matrix shown as block 952 in FIG. 14. The row addresses are provided on row lines 954 from row decoder/driver 922 which determines the row to be addressed by decoding the signals on row address lines 956. The microcontroller 675 then polls the state of each of the column lines 958 via input port 912. This technique for reading the states of a plurality of membrane-type buttons is well known and need not be further described here.

The back-illumination lights 864L, 866L, 868L, 870L and 724L are all shown within dotted lines 970 in the lower-right hand portion of FIG. 14. For convenient reference, these lights are represented as rectangles and are laid out in the same general format as is found in FIG. 9. The back-lit illumination lights, as previously explained, are located on the PC board 770 shown in FIG. 8. The illumination lights may be of any suitable type, including incandescent bulbs. In the preferred embodiment, however, a conventional bank of series-connected LEDs are used, as is shown by light 864aL. Although the other lights are indicated as rectangles, all of them employ a series-connected network of four diodes of the type shown by 864aL.

To turn on individual lights, microcontroller 675 loads up individual one-bit latch locations contained in the decoder/driver chips 924-1 through 924-4 which in turn sink current from the individual output lines 970. A three-line address bus 972 is used to address the respective latches 924a through 924d, after which data on line 973 is transferred in under the control signals provided on control bus 974. In this manner each one of the output lines 970 can be switched from an open-collector or high-impedance output state to a low-impedance grounded state. In this latter state, current is sunk to ground 976, which turns on the corresponding diode block. Current-limiting resistors 926 are provided to ensure that the diodes are not overloaded. Plus 12 volt DC power is provided via line 980 which is connected to each of the lights 724 and 864–870. These lights are connected to individual respective ones of the output lines 970 by conductors 982, such as is illustrated by conductor 982-1. Accordingly, the microcontroller 675 is capable of turning on and off the individual ones of the lights 724, 864–870 as desired or commanded to do by main processor 324.

The operation of the two pairs of optical sender/receiver circuits shown in the upper-left hand corner of FIG. 14 will now be explained. When the membrane switch assembly 707 is properly connected and the remote console 370 provided with power, LED 936 emits optical radiation 932, which may be of the visible or infrared variety. Only when legend card 780 is properly in place will the identification hole 888a allow the optical radiation 932 emitted by LED 936 to pass through to phototransistor 990, causing transistor 990 to conduct. This makes line 991 change from a near zero-volts state to a near plus five-volt state. The signal on line 991 is fed into the negative input of comparator 992, which may be a conventional operational amplifier, causing its output 993 to change from a higher voltage state near the $V_{cc}$ to a lower voltage state. Conductor 993 is wired into input port 914 of microcontroller 675 which detects this change in voltage, and thus knows that diode 936 is emitting light, and "anterior" legend card 180a is in place in controller 370. In a similar manner, the receiver circuit 930 has its output conductor 994 change from a high state to a low state only when card 780p is properly in place, so that radiation 934 from LED 938 will strike phototransistor 995 causing comparator 996 to change states. Since conductor 994 is wired directly to input port 914, this change of state is also observed by microcontroller 675.

The microcontroller 675 contains a stored program in EEPROM 906 for carrying out the necessary and periodic monitoring of all the elements of the membrane matrix switch 952 and the driving of the back-illumination lights 970. Armed with the foregoing functional description, the programming of a microprocessor for monitoring matrix switch assembly 952 and driving of a bank 970 of indicator lights is well within the skill of those in the art, and therefore need not be described here. Programming a microcontroller for serial data communications with a main processor are well known and need not be described beyond mentioning the following. In the preferred embodiment, the microcontroller continuously monitors the matrix switch 952 at a relatively high rate of speed and when a closure of any individual membrane switch 712 or 722 is detected, the switch is decoded into an 8-bit response code which is generated and transferred via the RS 422 bus to the serial communications interface 644 of the IO expansion board 352. Interface 644 causes the interrupt generator 646 to generate an interrupt request on line 374, thereby bringing the interrupt to the attention of processor 324. Processor 324 maintains a current state table in its RAM 325 indicating the status of each of the input switches of matrix 952. After a predetermined interval of time, all of the entries in the tables will be reset and active control through the remote control console 370 terminated if updating of the table in RAM 325 and/or periodic hand-shaking communications fail to take place between the processor 324 and microcontroller 675. In the manner, the processor 324 will not be left in a hung-up state or assume any button on remote console 370 remains pushed indefinitely in the event that communications with the remote consoles 370 is lost for any reason. Additionally, the microcontroller embodiment contains a "watchdog timer" circuit 903 shown in FIG. 14, that requires continual updating from the processor to insure the proper operation of the microcontroller. If the processor assumes a hung-up state, the timer forces a hardware reset of remote control.

VI. Epilogue

The foregoing detailed description shows that the preferred embodiments of the present invention are well suited to fulfill the objects above-stated. It is recognized that those skilled in the art may make various modifications or additions to the preferred embodiments chosen to illustrate the present invention without departing from the spirit and proper scope of the invention. For example, different electronic control circuits may be used within the remote control console to provide the necessary monitoring and illumination control functions. Also, different types of switches or buttons may be utilized. Further, either optical or radio communication channels may be used to pass information between the main console and the remote controller. Further, a remote control console employing a flat panel display, such as an electroluminescent display or liquid crystal display may be used to provide virtually full simulation of the display 50 if desired. Accordingly, it is to be understood that the protection sought and to be afforded hereby should be deemed to extend to the subject matter defined by the appended claims, including all fair equivalents thereof.

We claim:

1. A remote operator interface console for a microsurgical control system for operating a plurality of microsurgical instruments, said system having a main control console, said main control console having a main processor and a display screen for simultaneously displaying multiple fields of information associated with the microsurgical instruments, the remote console comprising:

communications means, connected to the main processor, for causing the remote console to communicate microsurgical operating function data with the control system; and display means, connected to the communication means, for simulating the display of at least part of the fields of information associated with the microsurgical instruments displayed on the display screen;

the display means includes a plurality of light emitting means, selectably activated by data transmitted from the main control console, for illuminating selected areas of a display region;

microcontroller means, connected to the light emitting means, for receiving the transmitted data and activating individual ones of the light emitting means in response thereto;

card means, removably placed over at least some of the light emitting means, for providing legends illuminated by passing emitted light from the emitting means therethrough to simulate the display of the information contained upon the display screen of the main console; and means for detecting compatibility of said card means with a preset operating condition of said control system and enabling said remote console when compatibility is detected.

2. A remote operator interface console for a microsurgical control system for operating a plurality of microsurgical instruments, said system having a main control console, said main control console having a main processor and a display screen for simultaneously displaying multiple fields of information associated with the microsurgical instruments, the remote console comprising:

communications means, connected to the main processor, for causing the remote console to communicate microsurgical operating function data with the control system; and display means, connected to the communication means, for simulating the display of at least part of the fields of information associated with the microsurgical instruments displayed on the display screen;

the display means includes a plurality of light emitting means, selectably activated by data transmitted from the main control console, for illuminating selected areas of a display region;

microcontroller means, connected to the light emitting means, for receiving the transmitted data and activating individual ones of the light emitting means in response thereto;

card means, removably placed over at least some of the light emitting means, for providing legends illuminated by passing emitted light form the emitting means therethrough to simulate the display of the information contained upon the display screen of the main console; and means for detecting compatibility of said card means with a predetermined alignment of actuators on said remote console.

3. A remote operator interface console for a microsurgical control system for operating a plurality of microsurgical instruments, said system having a main control console, said main control console having a main processor and a display screen for simultaneously displaying multiple fields of information associated with the microsurgical instruments, the remote console comprising:

communications means, connected to the main processor, for causing the remote console to communicate microsurgical operating function data with the control system; and display means, connected to the communication means, for simulating the display of at least part of the fields of information associated with the microsurgical instruments displayed on the display screen;

the display means includes a plurality of light emitting means, selectably activated by data transmitted from the main control console, for illuminating selected areas of a display region;

microcontroller means, connected to the light emitting means, for receiving the transmitted data and activating individual ones of the light emitting means in response thereto;

card means, removably placed over at least some of the light emitting means, for providing legends illuminated by passing emitted light from the emitting means therethrough to simulate the display of the information contained upon the display screen of the main console; and means for detecting compatibility of said card means with a predetermined alignment of illumination means for card identification in said remote console.

4. The remote console of claim 1 wherein said communication means comprises:
serial communication interface means, connected to the microsurgical control system, for receiving transmitted data from the remote console; and
interrupt generation means, connected to the serial communication interface means and to the main processor, for generating an interrupt signal to the main processor upon receipt of the transmitted data from the remote console.

5. The remote console of claim 1, further comprising:
switch means, connected to the microcontroller means, for modifying the displayed information upon the display screen of the main control console.

6. The remote console of claim 1, further comprising:
local switch means for enabling an operator to select surgical functions to be carried out by control equipment in the main console.

7. The remote console of claim 6, wherein:
the switch means includes a plurality of switches, with at least some of the switches being arranged adjacent to selected illuminated areas.

8. The remote console as defined in claim 2 wherein said communication means comprises:
serial communication interface means, connected to the microsurgical control system, for receiving transmitted data from the remote console; and
interrupt generation means, connected to the serial communication interface means and to the main processor, for generating an interrupt signal to the main processor upon receipt of the transmitted data from the remote console.

9. The remote console of claim 2, further comprising: switch means, connected to the microcontroller means, for modifying the displayed information upon the display screen of the main control console.

10. The remote console of claim 2, further comprising:
local switch means for enabling an operator to select surgical functions to be carried out by control equipment in the main console.

11. The remote console of claim 10, wherein:
the switch means includes a plurality of switches, with at least some of the switches being arranged adjacent to selected illuminated areas.

12. The remote console as defined in claim 3 wherein said communication means comprises:
serial communication interface means, connected to the microsurgical control system, for receiving transmitted data from the remote console; and
interrupt generation means, connected to the serial communication interface means and to the main processor, for generating an interrupt signal to the main processor upon receipt of the transmitted data from the remote console.

13. The remote console of claim 3, further comprising:
switch means, connected to the microcontroller means, for modifying the displayed information upon the display screen of the main control console.

14. The remote console of claim 3, further comprising:
local switch means for enabling an operator to select surgical functions to be carried out by control equipment in the main console.

15. The remote console of claim 14, wherein:
the switch means includes a plurality of switches, with at least some of the switches being arranged adjacent to selected illuminated areas.

* * * * *